(12) United States Patent
Estes

(10) Patent No.: US 11,260,169 B2
(45) Date of Patent: Mar. 1, 2022

(54) INFUSION PUMP SYSTEM AND METHODS

(71) Applicant: Bigfoot Biomedical, Inc., Milpitas, CA (US)

(72) Inventor: Mark C. Estes, Malibu, CA (US)

(73) Assignee: BIGFOOT BIOMEDICAL, INC., Milpitas, CA (US)

(*) Notice: Subject to any disclaimer, the term of this patent is extended or adjusted under 35 U.S.C. 154(b) by 606 days.

(21) Appl. No.: 15/904,855

(22) Filed: Feb. 26, 2018

(65) Prior Publication Data

US 2018/0177939 A1  Jun. 28, 2018

Related U.S. Application Data

(62) Division of application No. 13/828,773, filed on Mar. 14, 2013, now abandoned.

(51) Int. Cl.
  *A61M 5/142* (2006.01)
  *A61M 5/172* (2006.01)
  *A61M 5/145* (2006.01)

(52) U.S. Cl.
  CPC ....... *A61M 5/14244* (2013.01); *A61M 5/1452* (2013.01); *A61M 5/172* (2013.01); *A61M 2005/14268* (2013.01); *A61M 2205/18* (2013.01); *A61M 2205/3358* (2013.01); *A61M 2205/3368* (2013.01)

(58) Field of Classification Search
  CPC ............ A61M 31/002; A61M 5/14276; A61M 5/16831; A61M 2005/16863; A61M 2205/3372; A61M 5/14244; A61M 2005/14264
  See application file for complete search history.

(56) References Cited

U.S. PATENT DOCUMENTS

| | | | |
|---|---|---|---|
| 5,679,245 A | * | 10/1997 | Manica ............. A61M 1/16 210/134 |
| 6,126,595 A | | 10/2000 | Amano |
| 6,233,471 B1 | | 5/2001 | Berner et al. |
| 6,458,102 B1 | | 10/2002 | Mann et al. |
| 6,461,331 B1 | | 10/2002 | Van Antwerp |
| 6,474,219 B2 | | 11/2002 | Klitmose et al. |
| 6,485,461 B1 | | 11/2002 | Mason et al. |

(Continued)

FOREIGN PATENT DOCUMENTS

| CA | 2543545 | 5/2005 |
|---|---|---|
| DE | 196 27 619 A | 1/1998 |

(Continued)

OTHER PUBLICATIONS

MiniMed Paradigm Insulin Pump User Guide (Year: 2008).*

(Continued)

*Primary Examiner* — William R Carpenter
*Assistant Examiner* — William R Frehe
(74) *Attorney, Agent, or Firm* — Hamre, Schumann, Mueller & Larson, P.C.

(57) ABSTRACT

Some embodiments of an infusion pump system can provide an alarm and user instructions in response to an ambient air pressure change or ambient air temperature that exceeds an alarm limit parameter. In some circumstances, the infusion pump system can be configured to monitor the actual ambient air pressure and temperature around the infusion pump system.

16 Claims, 10 Drawing Sheets

(56) References Cited

U.S. PATENT DOCUMENTS

| | | |
|---|---|---|
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,572,542 B1 | 6/2003 | Houben |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,723,077 B2 | 4/2004 | Pickup et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe et al. |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0104982 A1 | 6/2003 | Wittmann et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Estes |
| 2005/0222645 A1 | 10/2005 | Malave et al. |
| 2005/0238507 A1 | 10/2005 | Dilanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |

(56) References Cited

U.S. PATENT DOCUMENTS

| | | |
|---|---|---|
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2008/0088731 A1 | 4/2008 | Tanaka et al. |
| 2008/0125700 A1 | 5/2008 | Moberg et al. |
| 2008/0172027 A1 | 7/2008 | Blomquist |
| 2008/0306444 A1 | 12/2008 | Brister |
| 2009/0069784 A1 | 3/2009 | Estes et al. |
| 2009/0088731 A1* | 4/2009 | Campbell ............ G06F 19/3468 604/890.1 |
| 2009/0088690 A1 | 5/2009 | Carter et al. |
| 2009/0149743 A1* | 6/2009 | Barron .............. A61M 5/16827 600/431 |
| 2009/0177142 A1 | 7/2009 | Blomquist et al. |
| 2009/0221914 A1* | 9/2009 | Barrett .................. A61M 5/007 600/431 |
| 2009/0270844 A1 | 10/2009 | Seeley et al. |
| 2010/0198187 A1 | 8/2010 | Yodfat et al. |
| 2010/0331779 A1* | 12/2010 | Nystrom ............... A61M 5/365 604/125 |
| 2011/0040251 A1 | 2/2011 | Blomquist et al. |
| 2011/0043357 A1* | 2/2011 | Peatfield ............. A61M 5/1413 340/522 |
| 2011/0193704 A1* | 8/2011 | Harper .................. A61B 5/145 340/573.1 |
| 2011/0218516 A1 | 9/2011 | Grigorov |
| 2012/0035543 A1* | 2/2012 | Kamen ................. A61M 5/385 604/113 |
| 2012/0185267 A1 | 7/2012 | Kamen |

FOREIGN PATENT DOCUMENTS

| | | |
|---|---|---|
| DE | 102 36 669 | 2/2004 |
| DE | 20 2005 012 358 | 10/2005 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 04/056412 | 7/2004 |
| WO | WO 2004/093648 | 11/2004 |
| WO | WO 04/110526 | 12/2004 |
| WO | WO 05/002652 | 1/2005 |
| WO | WO 05/039673 | 5/2005 |
| WO | WO 05/072794 | 8/2005 |
| WO | WO 05/072795 | 8/2005 |
| WO | WO 2006/075016 | 7/2006 |
| WO | WO 06/105792 | 10/2006 |
| WO | WO 06/105793 | 10/2006 |
| WO | WO 06/105794 | 10/2006 |
| WO | WO 2011/097487 | 8/2011 |

OTHER PUBLICATIONS

Asante Pearl, Insulin Pump User Manual, 2012, 180 pages.
Collins and Lee, "Microfluidic flow transducer based on the measurement of electrical admittance," *Lab Chip*, 2003, 12 pages.
Debiotech News Release, "Debiotech reveals its new miniaturized Disposable Insulin Nanopump™ for Diabetes therapy," available at http://www.debiotech.com/news/nw_159.html Apr. 24, 2006, 3 pages.
International Search Report and Written Opinion in International Application No. PCT/US2014/021934, dated Oct. 30, 2014, 13 pages.
Medtronic News Release, "Medtronic Receives FDA Approval for World's First Insulin Pump with Real-time Continuous Glucose Monitoring," Apr. 13, 2006, 3 pages.
Patent Abstracts of Japan, vol. 1999, No. 04, and JP 11 010036, Apr. 30, 1999 and Jan. 19, 1999, Toray Ind. Inc., 6 pages.
Supplementary European Search Report in Application No. 14774894, dated Oct. 31, 2016, 4 pages.
Walsh et al., "Guidelines for Insulin Dosing in Continuous Subcutaneious Insulin Infusion Using New Formulas from a Retrospective Study of Individuals with Optimal Glucose Levels", *J. Diabetes Science and Technology*, Sep. 2010, 4(5):8 pages.
Walsh et al.,"Guidelines for Optimal Bolus Calculator Settings in Adults", *J. Diabetes Science and Technology*, Jan. 2011, 5(1):7 pages.

* cited by examiner

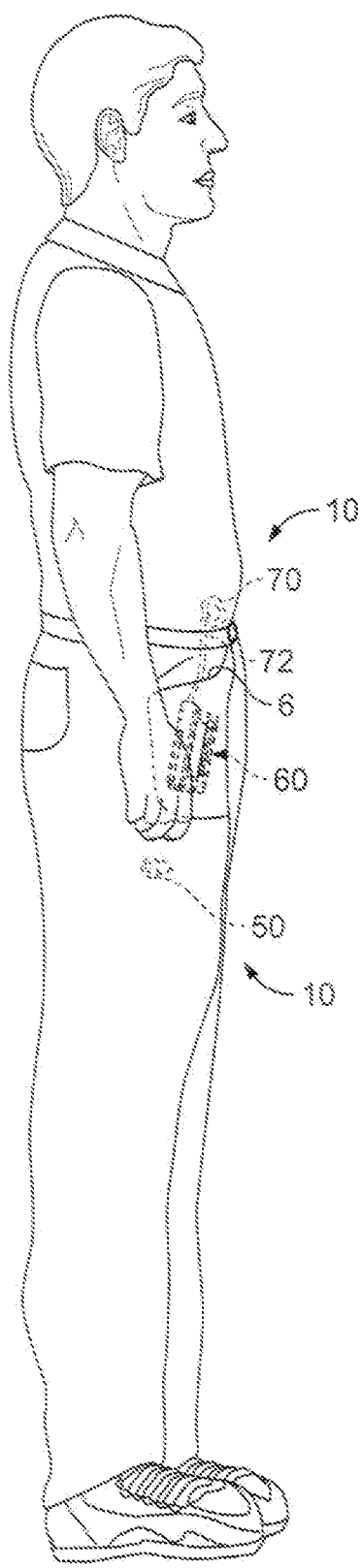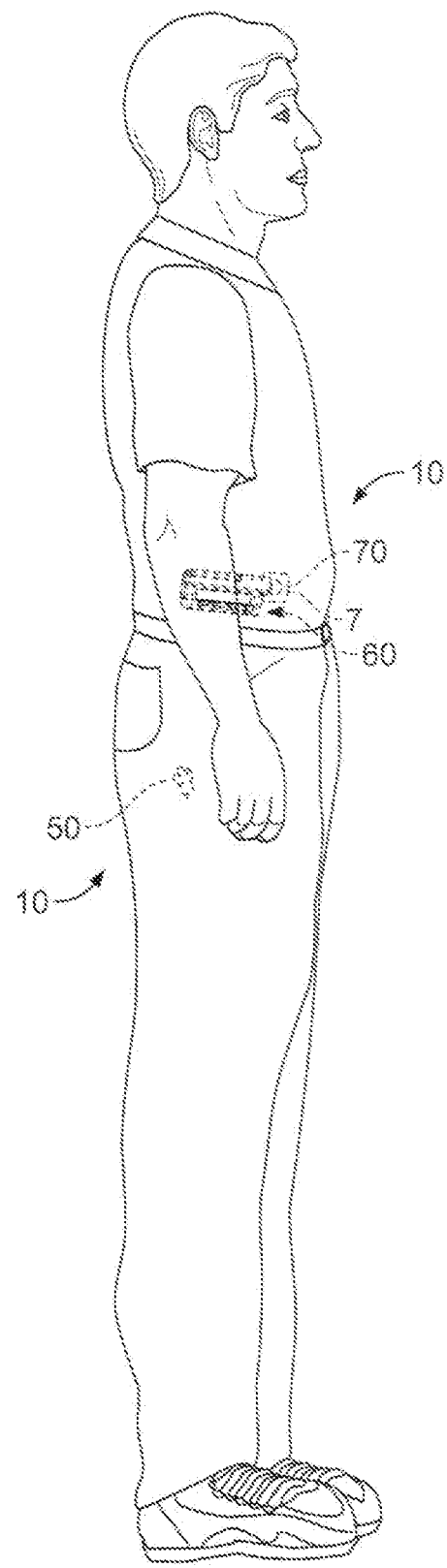
FIG. 3
FIG. 4

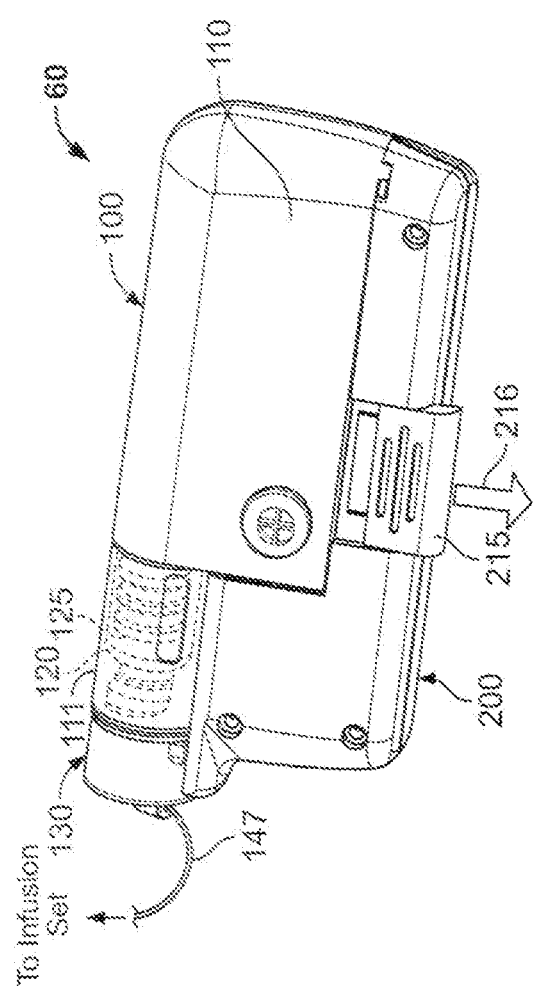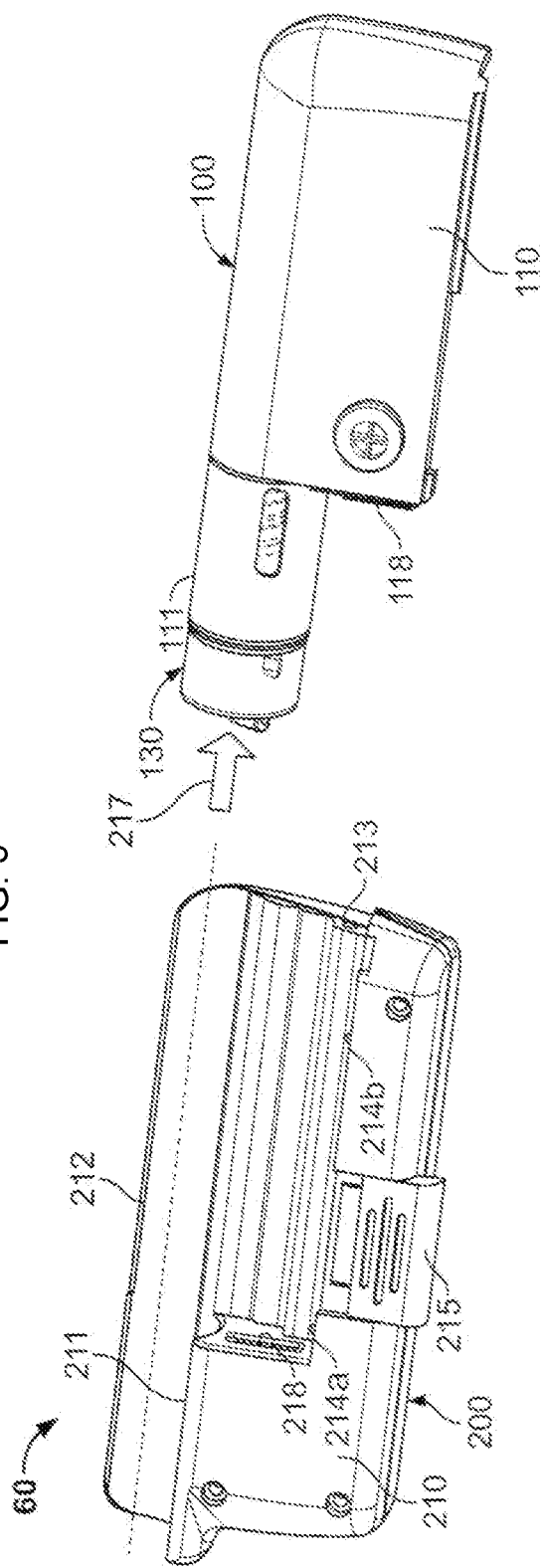
FIG. 5
FIG. 6

INFUSION PUMP SYSTEM AND METHODS

CROSS-REFERENCE TO RELATED APPLICATIONS

This application is a divisional application of and claims priority to U.S. application Ser. No. 13/828,773, filed on Mar. 14, 2013.

TECHNICAL FIELD

This disclosure relates to portable infusion pump systems to deliver fluids, such as insulin infusion pump systems or the like.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood glucose levels.

Ambient air pressure changes can have an effect on the operation of medical infusion pump devices. For example, in some circumstances an ambient air pressure reduction can initiate bubble formation in the liquid medicine within the pump device. The presence of bubbles in the medicine can thereafter negatively affect the accuracy of the medicine dispensations from the medical infusion pump or may cause air bubbles to be infused into the user.

In some cases, ambient air temperatures changes can have a negative effect on the medicine dispensed by a medical infusion pump. For example, if insulin is exposed to freezing temperatures or temperatures substantially above body temperature for a particular period of time, the insulin can become less effective or otherwise require replacement.

SUMMARY

Some embodiments of an infusion pump system can provide an alarm (e.g., an alert, a safety alarm, or the like) and initiate or suggest countermeasures in response to an ambient air pressure change or an ambient air temperature that exceeds an alarm limit parameter. In some circumstances, the infusion pump system can be configured to monitor the actual ambient air pressure and temperature around the infusion pump system. The infusion pump system can compare the actual ambient air pressure and temperature to alarm limits and provide an alarm when a limit is exceeded. In some circumstances, both "high" and "low" ambient air pressure and temperature alarm limits can be established.

In particular embodiments described herein, a medical infusion pump system may include a portable pump housing that receives an insulin supply for dispensation to a user. The pump housing may at least partially contain a pump drive system to dispense insulin from the insulin supply through a flow path to the user. The system may also include a controller that communicates with the pump drive system to dispense the insulin from the portable pump housing. Optionally, the controller may include a user interface display device. The system may further include pressure detection device that communicates with the controller. The controller, in response to a detected ambient air pressure level being less than a lower threshold value or greater than a higher threshold value, can be configured to output an alarm and output a textual instruction via the user interface display indicative of maintaining the same insulin supply for subsequent dispensation.

In some embodiments described herein, a medical infusion pump system includes a portable pump housing that receives insulin for dispensation to a user. The pump housing may at least partially contain a pump drive system to dispense the insulin through a flow path to the user. The system may further include a controller that communicates with the pump drive system to dispense the insulin from the portable pump housing. The system may also include a temperature detection device that communicates with the controller. The controller, in response to a detected temperature level being less than a lower threshold value or greater than a higher threshold value, can be configured to output an alarm.

In various embodiments, a medical infusion pump system may include a portable pump housing defining an opening that slidably receives a prefilled cartridge of insulin for dispensation to a user. The pump housing may at least partially contain a pump drive system to dispense the insulin through a flow path to the user. The system may also include a controller that communicates with the pump drive system to dispense the insulin from the portable pump housing. The system may further include a detection device that communicates with the controller, and the detection device may be configured to detect an indicator on the prefilled cartridge of insulin that indicates whether the prefilled cartridge has sustained a particular temperature exposure level. The controller, in response to a detection of the indicator that the prefilled cartridge has sustained the particular temperature exposure level, may be configured to output an alarm.

Particular implementations described herein include a method of operating an insulin infusion pump system. The method may include receiving, at a controller of an insulin infusion pump system, ambient air pressure information indicative of an ambient air pressure external of the insulin infusion pump system. The method may also include determining if the ambient air pressure information is less than a low limit threshold value or greater than a high limit threshold value. The low and high limit threshold values may be stored in the memory of the controller. The method may further include, in response to determining the ambient air pressure information is less than the low limit threshold value or greater than the high limit threshold value, outputting (i) an alarm and (ii) user instructions for continuing operations of the insulin infusion pump system without replacing an insulin supply and components of the infusion pump system.

In some implementations described herein, a method of operating an insulin infusion pump system can include the step of receiving, at a controller of an insulin infusion pump system, temperature information indicative of a temperature at the insulin infusion pump system. The method may further include determining, by the controller, if the temperature information is less than a low limit threshold value or greater than a high limit threshold value. The low and high limit threshold values may be stored in the memory of the controller. The method may also include outputting, by the controller, an alarm in response to determining the temperature information is less than the lower threshold value or greater than the higher threshold value.

In some embodiments described herein, a medical infusion pump system may include a portable pump housing that receives a medicine supply for dispensation to a user. The pump housing may at least partially contain a pump drive system to dispense medicine from the medicine supply through a flow path to the user. The system may also include a controller that communicates with the pump drive system to dispense the medicine from the portable pump housing. Furthermore, the system may include at least one of a pressure detection device and a temperature detection device configured to be coupled to the portable pump housing and to communicate with the controller.

Some of the embodiments described herein may provide one or more of the following advantages. First, some embodiments of the infusion pump system can be configured to detect an ambient air pressure or ambient air temperature that exceeds an alarm limit parameter, and to thereafter provide readily understandable instructions (via a user interface) to the user for which types of corrective measures should be taken. For example, the user interface of the infusion pump system can be configured to output different instructions to the user depending on type of ambient pressure change or ambient air temperature that was detected.

Second, some embodiments of the infusion pump system may provide an alert with instructions that prompts the user to take preventive or corrective actions that enable the user to maintain the efficacy of treatment provided by the infusion pump system. For example, in response to a "low" ambient air pressure (that induces a detection of a pressure drop) the infusion pump system may provide instructions to the user to inspect for bubbles in the medicine and to take a blood glucose measurement. Such infusion pump system features can be used advantageously to maintain the user's blood glucose level within a desired range despite the exposure of the infusion pump system to deviations in ambient conditions.

Third, particular embodiments of an infusion pump system may prevent use of a medicine supply that may have deteriorated or otherwise become less effective. For example, in response to a "high" ambient air temperature the infusion pump system may provide instructions to the user to replace the medicine cartridge because the high temperature may have reduced the medicine's efficacy. In some circumstances, infusion pump system may prevent dispensation of the medicine that was subjected to the "high" ambient air temperature for an extended period of time.

Fourth, the infusion pump system may be configured to be portable, wearable, and (in some circumstances) concealable. For example, a user can conveniently wear the infusion pump system on the user's skin under clothing or can carry the pump system in the user's pocket (or other portable location) while receiving the medicine dispensed from the pump device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a perspective view of the infusion pump system of FIG. 1 in which the pump assembly is worn on clothing of a user, in accordance with particular embodiments.

FIG. 4 is a perspective view of an infusion pump system of FIG. 1 in which the pump assembly is worn on skin of a user, in accordance with other embodiments.

FIGS. 5-6 are perspective views of a pump device being detached from a controller device of the system of FIG. 1, in accordance with some embodiments.

Like reference symbols in the various drawings indicate like elements.

DETAILED DESCRIPTION OF ILLUSTRATIVE EMBODIMENTS

Figure 1:
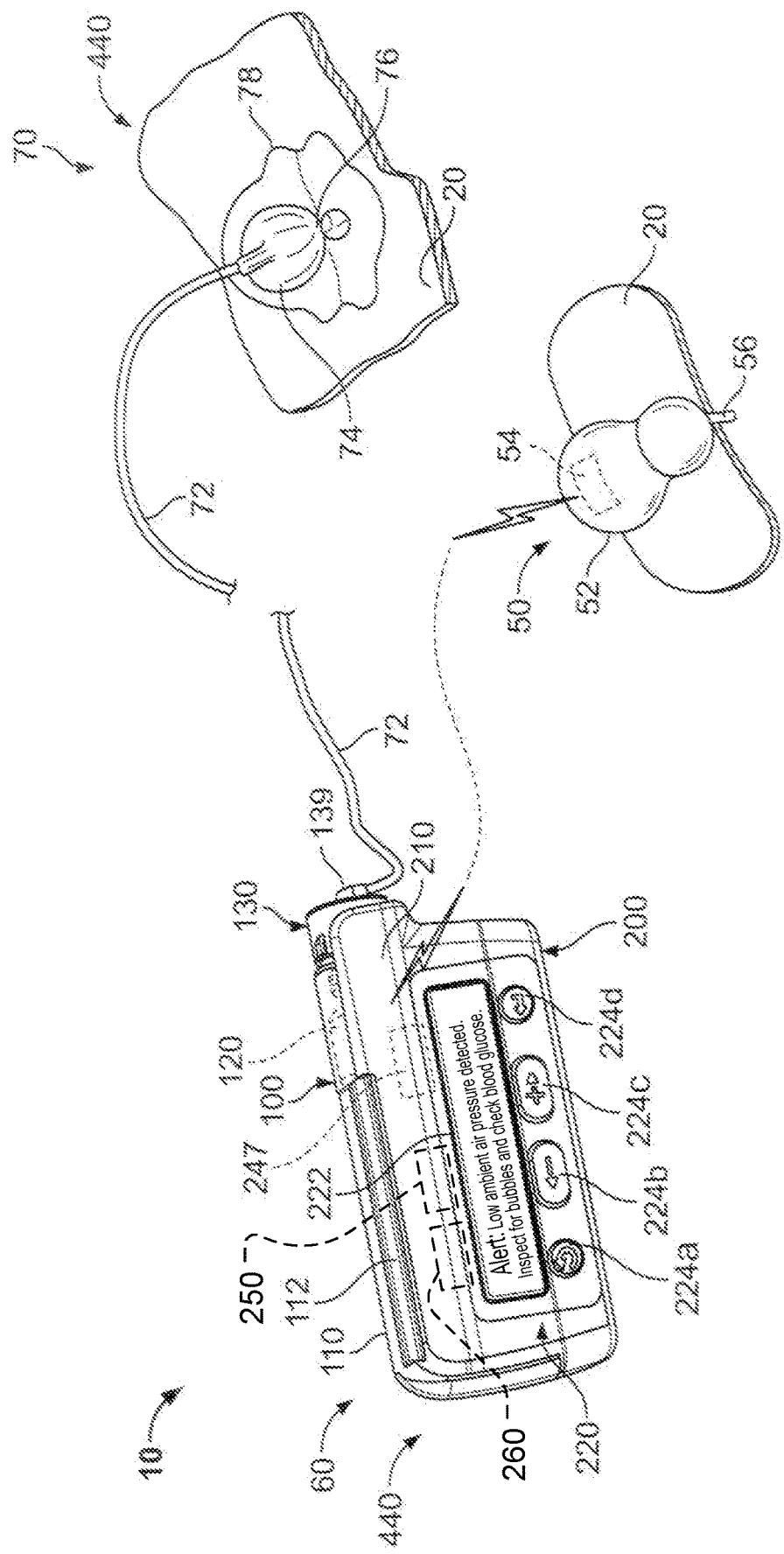
FIG. 1 is a perspective view of an infusion pump system, in accordance with some embodiments.

Referring to FIG. 1, an infusion pump system 10 can include a pump assembly 60 used to supply insulin or other medication to a user via, for example, an infusion set 70. In some embodiments, the infusion pump system 10 can be configured to supply scheduled basal dosages of insulin (or other medication) along with user-selected bolus dosages. The basal rate can be selected to maintain a user's blood glucose level in a target range during normal activity when the user is not eating or otherwise consuming food items. The selected bolus deliveries may provide substantially larger amounts of insulin to limit the blood glucose level during certain circumstances, such as the consumption of carbohydrates and other food items (e.g., a "meal bolus") or to lower an elevated glucose level (e.g., a "correction bolus").

In some embodiments, a glucose monitoring device 50 can be in communication with the infusion pump assembly 60 for the purpose of supplying data indicative of a user's blood glucose level to a controller device 200 included in the pump assembly 60. The infusion pump system 10 can utilize the data indicative of a user's blood glucose level to, for example, provide an alarm (e.g., an audible or textual safety alarm, an audible or textual alert notification, or another type of alarm) when the user's blood glucose level falls below a low glucose alarm limit or rises above a high glucose alarm limit.

In some embodiments, as described further below in connection with FIGS. 12 and 13, the infusion pump system 10 can monitor actual ambient conditions such as air pressure and temperature. In some such embodiments, the infusion pump system 10 can include an air pressure sensor 250 and/or a temperature sensor 260 that can measure the ambient pressure and temperature conditions respectively. The pressure sensor 250 and temperature sensor 260 can be in electrical communication with the controller device 200. The controller device 200 can provide an alarm (e.g., an audible or textual safety alarm, an audible or textual alert notification, or another type of alarm) when the measured ambient conditions exceed predetermined alarm limits. In addition to alarming, in some embodiments the controller device 200 can provide instructions for the user to take actions to counteract the potential negative effects that the ambient conditions may have on the accuracy of the infusion pump system 10. By implementing the instructions, the user's blood glucose level can be maintained within a desired range despite the exposure of the infusion pump system 10 to deviations in ambient conditions.

Figure 2:
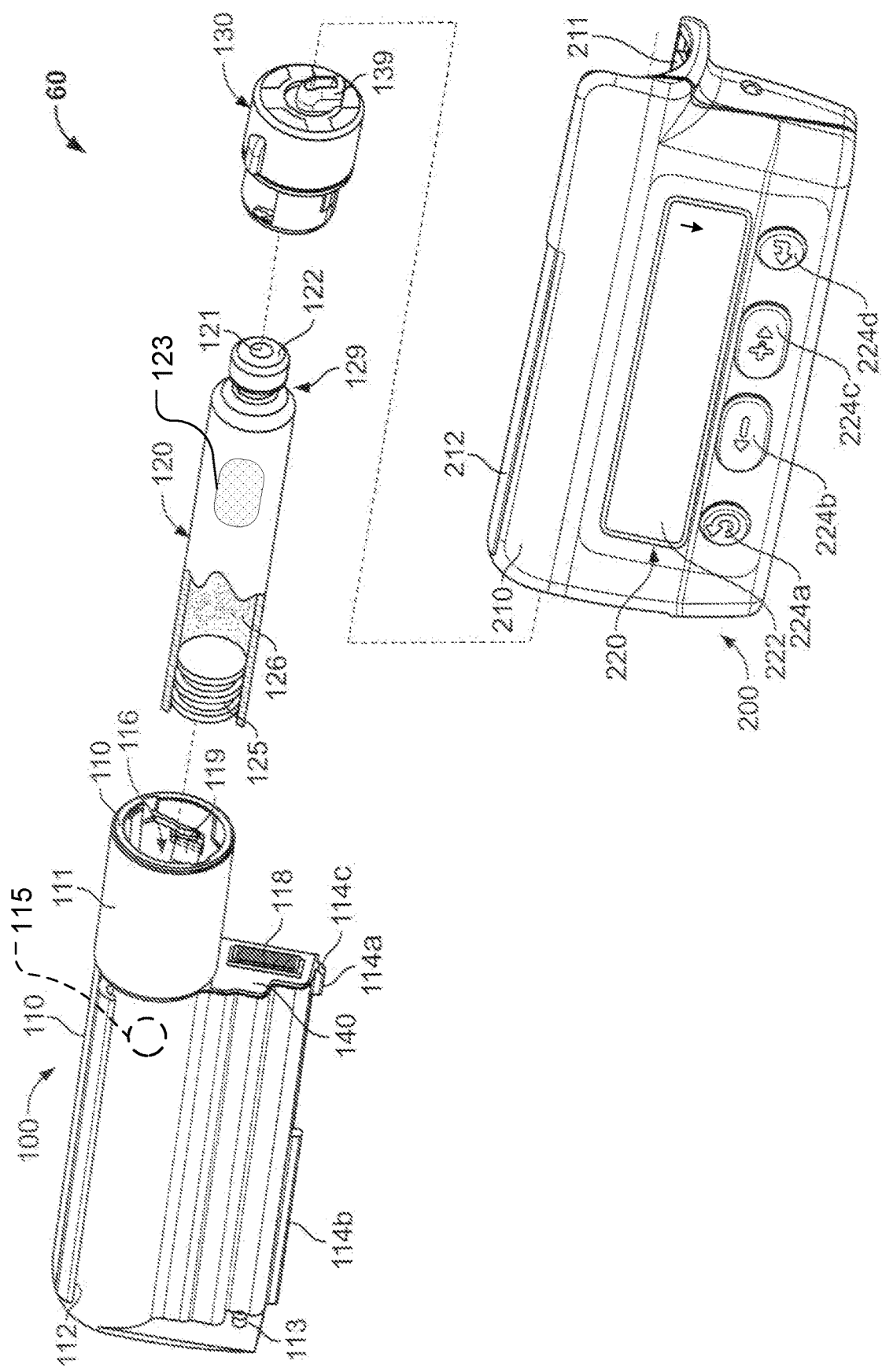
FIG. 2 is a perspective exploded view of an infusion pump assembly of the system of FIG. 1.

Referring now to FIGS. 1-2, the infusion pump assembly 60 can include a pump device 100 and the controller device 200 that communicates with the pump device 100. The pump device 100 includes a housing structure 110 that defines a cavity 116 in which a fluid cartridge 120 can be received. The pump device 100 also includes a cap device 130 to retain the fluid cartridge 120 in the cavity 116 of the housing structure 110. The pump device 100 includes a drive system (described in more detail below in connection with FIG. 10) that advances a plunger 125 in the fluid cartridge 120 so as to dispense fluid therefrom. In some embodiments, the dispensed fluid exits the fluid cartridge 120, passes through a flexible tube 72 of the infusion set 70 to a cannula housing 74. The dispensed fluid can enter through the skin via a cannula 76 attached to the underside of the cannula housing 74.

In some embodiments, the controller device 200 communicates with the pump device 100 to control the operation of the pump drive system. When the controller device 200, the pump device 100 (including the cap device 130 in this embodiment), and the fluid cartridge 120 are assembled together, the user may conveniently wear the infusion pump assembly 60 on the user's skin under clothing or in the user's pocket while receiving the fluid dispensed from the pump device 100 (refer, for example, to FIGS. 3-4). Thus, in some embodiments, the pump assembly can operate as a portable unit that provides reliable delivery of insulin or another medication in a discrete manner.

As described in more detail below, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device 100 to the reusable controller device 200 for the dispensation of fluid from a new fluid cartridge 120. Accordingly, the user is permitted to reuse the controller device 200 (which may include complex or valuable electronics) while disposing of the relatively low-cost pump device 100 after each use. Such a pump assembly 60 can provide enhanced user safety as a new pump device 100 (and drive system therein) is employed with each new fluid cartridge 120.

Briefly, in use, the pump device 100 can be configured to removably attach to the controller device 200 in a manner that provides a secure fitting, an overall compact size, and a reliable electrical connection. The compact size permits the infusion pump assembly 60 to be discrete and portable. As described in more detail below, the controller device 200 of the infusion pump system can be used to provide glucose alarms indicative of high and low blood glucose levels (when compared to predetermined high and low blood glucose alarm levels, respectively) and to provide alarms related to measured ambient conditions such as air pressure and temperature (when compared to predetermined high and low pressure and temperature alarm levels, respectively).

Figure 11:
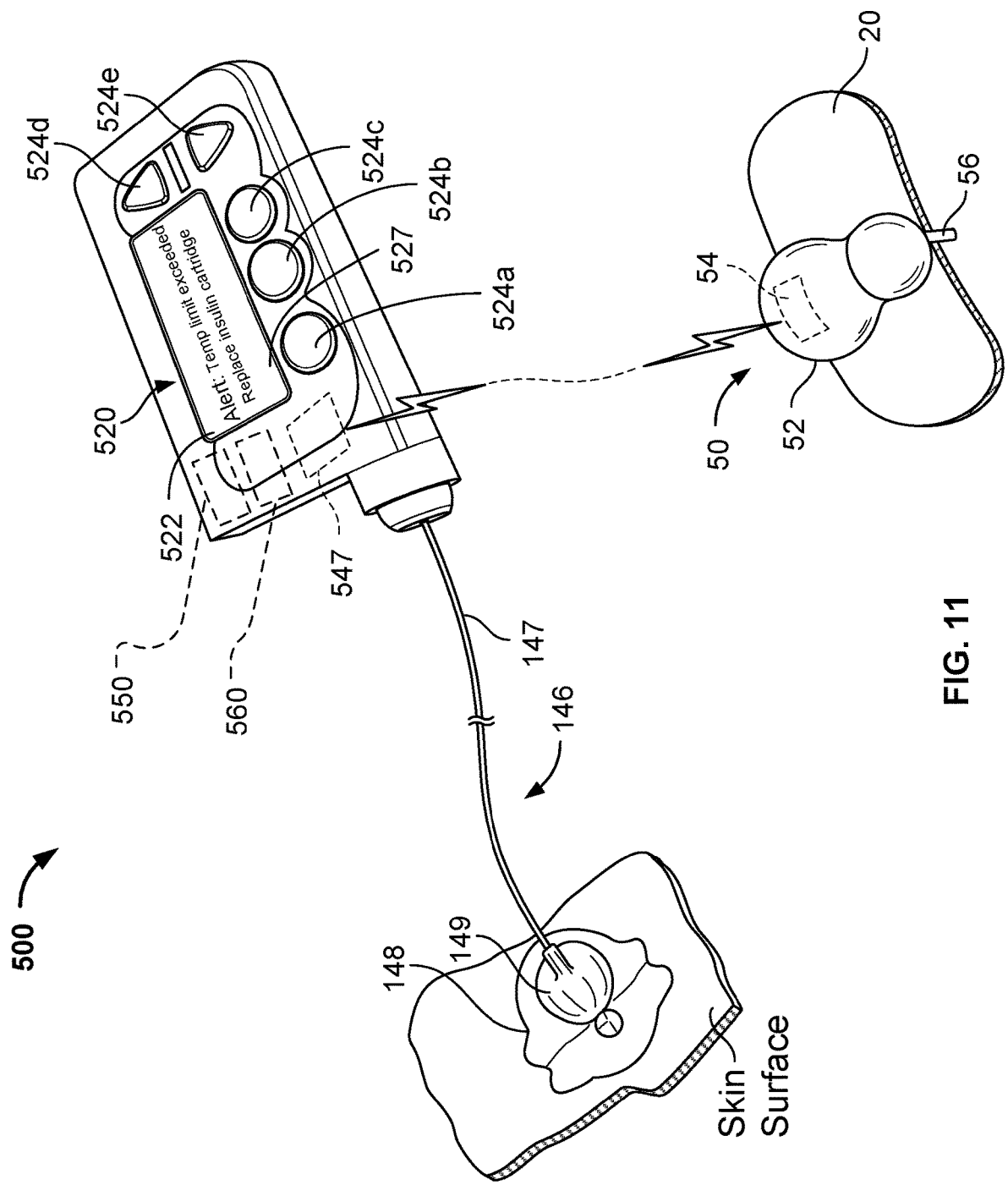
FIG. 11 is a perspective view of another example infusion pump system, in accordance with some embodiments.

It should be understood that, in alternative embodiments, the pump device 100 and the controller device 200 can be configured as a single unit in which the control components and the pump drive system are arranged in a single housing (refer, for example, to FIG. 11). In these alternative embodiments, the pump assembly (including the controller device and the pump device) may have a different size and shape and may operate as a reusable unit that can communicate with a number of monitoring devices 50 over a period of time.

Referring again to FIGS. 1-2, in some embodiments, the pump system 10 is a medical infusion pump system that is configured to controllably dispense a medicine from the cartridge 120. As such, the fluid cartridge 120 may contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: medicines to treat primary immune deficiency (e.g., Vivaglobin® by CSL Behring of King of Prussia, Pa.), pain relief drugs, hormone therapy, blood pressure treatments, antiemetics, osteoporosis treatments, or other injectable medicines.

It should be understood from the description herein that the fluid cartridge 120 may have a configuration other than that depicted in FIG. 2. For example, the fluid cartridge may have a different outer shape or a different reservoir volume. In another example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received).

In some embodiments, the fluid cartridge 120 may include features for indicating if the fluid cartridge 120 has been exposed to environmental conditions that may have reduced the efficacy of the contents. The basis for such features is the fact that high or low temperatures may reduce the effectiveness or potency of the medicine. Insulin, for example, may become tainted (less effective than normal) as a result of exposure to temperatures at or below freezing (about 0 degrees Celsius), or temperatures at or above human body temperatures (about 37 degrees Celsius). Therefore, an allowed temperature range for insulin can, in some cases, be from about 0 degrees to about 37 degrees Celsius. Other medicines may have other allowed temperature ranges. If the temperature indicators on the fluid cartridge 120 indicate that temperature limits have been exceeded, the fluid cartridge 120 can be discarded by the user or, in some embodiments, prevented from use by the infusion pump system 10.

In some embodiments, the fluid cartridge 120 can include one or more temperature sensitive ink labels 123 on the surface of the fluid cartridge 120, or on the packaging materials for the fluid cartridge 120. In some such embodiments, the temperature sensitive ink labels 123 can indicate whether the fluid cartridge 120 has been exposed to high or low temperature conditions that may have reduced the effectiveness or potency of the medicine. In some embodiments, the temperature sensitive ink, which may be in the form of a barcode in some embodiments, will become visually altered (e.g., the ink will become visible, or will become darkened, or will change color) in response to exceeding a high temperature limit or falling below a low temperature limit. In such cases, the user can visually perceive that the temperature sensitive ink labels 123 indicate that the fluid cartridge 120 has gone out of the allowed temperature range, and the user can discard the potentially tainted fluid cartridge 120 prior to installing it a pump device 100.

In some embodiments, the infusion pump system 10 can include an optical sensor 115 to detect the status of the temperature sensitive ink labels 123. The optical sensor 115 can be in electrical communication with the controller device 200. If the optical sensor 115 in conjunction with the controller device 200 detects an indication by the temperature sensitive ink labels 123 that the fluid cartridge 120 has gone out of the allowed temperature range, in some embodiments the infusion pump system 10 can initiate appropriate action such as providing an alarm, providing a message to the user, and ceasing dispensations of the medicine from the suspect fluid cartridge 120. In some embodiments, the optical sensor 115 can provide an initial detection of the temperature sensitive ink labels 123 when the pump device 100 containing the fluid cartridge 120 is first coupled with the controller device 200. In some embodiments, the optical sensor 115 can provide on-going monitoring of the temperature sensitive ink labels 123 while the infusion pump system 10 is in use. In some embodiments, both the initial detection and the on-going monitoring of the temperature sensitive ink labels 123 can be performed by the optical sensor 115 in conjunction with the controller device 200.

In some embodiments, the pump device 100 may include one or more structures that interfere with the removal of the medicine cartridge 120 after the medicine cartridge 120 is inserted into the cavity 116. For example, as shown in FIG. 2, the pump housing structure 110 may include one or more retainer wings 119 that at least partially extend into the cavity 116 to engage a portion of the medicine cartridge 120 when the medicine cartridge 120 is installed therein. In this embodiment, the pump housing structure 110 includes a pair of opposing retainer wings 119 (only one is shown in the view in FIG. 2) that flex toward the inner surface of the cavity 116 during insertion of the medicine cartridge 120. After the medicine cartridge is inserted to a particular depth, the retainer wings 119 are biased to flex outward (toward the center of the cavity 116) so that the retainer wings 119 engage a neck portion 129 of the medicine cartridge 120. This engagement with the retainer wings 119 and the neck portion 129 hinder any attempts to remove the medicine cartridge 120 away from the pump device 100. Alternative embodiments can include other features and/or configurations to hinder the removal of the medicine cartridge 120.

Embodiments of the pump device 100 that hinder the removal of the medicine cartridge 120 may facilitate the "one-time-use" feature of the pump device 100. Because the retainer wings 119 can interfere with attempts to remove the medicine cartridge 120 from the pump device 100, the pump device 100 will be discarded along with the medicine cartridge 120 after the medicine cartridge 120 is emptied, expired, or otherwise exhausted. The retainer wings 119 may serve to hinder attempts to remove the exhausted medicine cartridge 120 and to insert a new medicine cartridge 120 into the previously used pump device 100. Accordingly, the pump device 100 may operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-2, the cap device 130 can be joined with the pump device 100 after the medicine cartridge is inserted in the cavity 116. It should be understood that the cap device 130 may supplement or replace the previously described retainer wings 119 by locking into position after joining with the pump housing 110, thereby hindering removal of the fluid cartridge 120 in the pump housing 110. As shown in FIGS. 1-2, the cap device 130 may include an output port 139 that connects with the tubing 72 for dispensation of the medicine to the user. In some embodiments, the output port 139 may have an angled orientation such that a portion of the tubing extends transversely to the central axis of the cartridge 120 and cap device 130. The output port 139 can be configured to mate with tubing 72 of the infusion set 70 (FIG. 1).

In some embodiments, the controller device 200 may be removably attached to the pump device 100 so that the two components are mechanically mounted to one another in a fixed relationship. Such a mechanical mounting can form an electrical connection between the removable controller device 200 and the pump device 100. For example, the controller device 200 may be in electrical communication with a portion of a drive system (described in connection with FIG. 10) of the pump device 100. As described in more detail below, the pump device 100 includes a drive system that causes controlled dispensation of the medicine or other fluid from the cartridge 120. In some embodiments, the drive system incrementally advances a piston rod longitudinally into the cartridge 120 so that the fluid is forced out of an output end 122. The septum 121 at the output end 122 of the fluid cartridge 120 can be pierced to permit fluid outflow when the cap device 130 is connected to the pump housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

The controller device 200 may be configured to removably attach to the pump device 100, for example, in a side-by-side arrangement. The compact size permits the infusion pump assembly 60 to be discrete and portable when the pump device 100 is attached with the controller device 200 (as shown in FIG. 1). In this embodiment, the controller device 200 includes a controller housing structure 210 having a number of features that are configured to mate with complementary features of the pump housing structure 110 so as to form a releasable mechanical connection (described below in more detail in connection with FIGS. 5-7). Such mating features of the pump housing structure 110 and the controller housing structure 210 can provide a secure connection when the controller device 200 is attached to the pump device 100

As shown in FIG. 2, the pump device 100 may include an electrical connector 118 (e.g., having conductive pads, pins, or the like) that are exposed to the controller device 200 and that mate with a complementary electrical connector (refer to connector 218 in FIG. 6) on the adjacent face of the controller device 200. The electrical connectors 118 and 218 provide the electrical communication between the control circuitry (refer, for example, to FIG. 9) housed in the controller device 200 and at least a portion of the drive system or other components of the pump device 100. In some exemplary embodiments, the electrical connectors 118 and 218 permit the transmission of electrical control signals to the pump device 100 and the reception of feedback signals (e.g., sensor signals) from particular components within the pump device 100. Furthermore, as described in more detail below, the infusion pump assembly 60 may include a gasket 140 that provides a seal which is resistant to migration of external contaminants when the pump device 100 is attached to the controller device 200. Thus, in some embodiments, the pump device 100 and the controller device 200 can be assembled into a water resistant configuration that protects the electrical interconnection from water migration (e.g., if the user encounters water while carrying the pump assembly 60).

Referring again to FIGS. 1-2, the controller device 200 includes the user interface 220 that permits a user to monitor the operation of the pump device 100. In some embodiments, the user interface 220 includes a display 222 and one or more user-selectable buttons (e.g., four buttons 224a, 224b, 224c, and 224d in this embodiment). The display 222 may include an active area in which numerals, text, symbols, images, or a combination thereof can be displayed. For example, the display 222 may be used to communicate a number of status indicators, alarms, settings, and/or menu options for the infusion pump system 10. In some embodiments, the display 222 can present alarms related to various detected ambient conditions such as: a high or low ambient air pressure status; a high or low ambient temperature status; rising or falling ambient pressure or temperature levels (e.g., a noteworthy change in pressure or temperature), or any combination thereof. In the example depicted in FIG. 1, the display 222 indicates an alert in which the controller device 200 has sensed a low ambient air pressure (below a predetermined threshold level). In this embodiment, the display 222 also prompts the user to take particular countermeasures (as described further in reference to FIGS. 12 and 13), such as inspecting for bubbles and checking blood glucose, thereby helping the user to maintain blood glucose levels within the normal range.

In some embodiments, the user may press one or more of the buttons 224a, 224b, 224c, and 224d to shuffle through a number of menus or program screens that show particular status indicators, settings, and/or data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time.

The display 222 of the user interface 220 may be configured to display alarm information when no buttons 224a, 224b, 224c, and 224d have been pressed. For example, as shown in FIG. 1, the active area of the display 222 can display an alert indicating that the pressure sensor 250 of the controller device 200 has detected a low ambient air pressure (below a predetermined threshold level). This information can be displayed until one of the buttons 224a, 224b, 224c, and 224d has been actuated. This, or other, information can also be displayed for a period of time after no button 224a, 224b, 224c, and 224d has been actuated (e.g., five seconds, 10 seconds, 30 seconds, 1 minute, 5 minutes, or the like). Thereafter, the display 222 may enter sleep mode in which the active area is blank, thereby conserving battery power. In addition or in the alternative, the active area can display particular device settings, such as the current dispensation rate or the total medicine dispensed, for a period of time after no button 224a, 224b, 224c, or 224d has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224a, 224b, 224c, or 224d has been actuated (e.g., after 15 seconds or the like), and then the display 22 can enter sleep mode and become blank after a second period of time in which no button 224a, 224b, 224c, or 224d has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the display 222 of the controller device 200. Such monitoring capabilities may provide comfort to a user who may have urgent questions about the current operation of the pump device 100 (e.g., the user may be unable to receive immediate answers if wearing an infusion pump device having no user interface attached thereto). Moreover, the ambient condition alerts can be displayed contemporaneously with the detected blood glucose value, so the user is provided with the opportunity to make informed decisions regarding the current and future status of his or her blood glucose level.

Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200 without the requirement of locating and operating a separate monitoring module.

In other embodiments, the user interface 200 is not limited to the display and buttons depicted in FIGS. 1-2. For example, in some embodiments, the user interface 220 may include only one button or may include a greater numbers of buttons, such as two buttons three buttons, four buttons, five buttons, or more. In another example, the user interface 220 of the controller device 200 may include a touch screen so that a user may select buttons defined by the active area of the touch screen display. Alternatively, the user interface 220 may comprise audio inputs or outputs so that a user can monitor the operation of the pump device 100.

Referring to FIGS. 3-4, the infusion pump system 10 may be configured to be portable and can be wearable and concealable. For example, a user can conveniently wear the infusion pump assembly 60 on the user's skin (e.g., skin adhesive) underneath the user's clothing or carry the pump assembly 60 in the user's pocket (or other portable location) while receiving the medicine dispensed from the pump device 100. The pump device 100 may be arranged in a compact manner so that the pump device 100 has a reduced length. For example, in the circumstances in which the medicine cartridge 120 has a length of about 7 cm or less, about 6 cm to about 7 cm, and about 6.4 cm in one embodiment, the overall length of the pump housing structure 110 (which contains medicine cartridge and the drive system) can be about 10 cm or less, about 7 cm to about 9 cm, and about 8.3 cm in one embodiment. In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump assembly 60 (including the removable controller device 200 attached to the pump device 100 having the cap 130) may have an overall length of about 11 cm or less, about 7 cm to about 10 cm, and about 9.6 cm in one embodiment; an overall height of about 6 cm or less, about 2 cm to about 5 cm, and about 4.3 cm in one embodiment; and an overall thickness of about 20 mm or less, about 8 mm to about 20 mm, and about 18.3 mm in one embodiment.

The pump system 10 is shown in FIGS. 3-4 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 may be configured to mate with the infusion set 70. In general, the infusion set 70 is tubing system that connects the infusion pump system 10 to the tissue or vasculature of the user (e.g., to deliver medicine into the user's subcutaneous tissue or vasculature). The infusion set 70 may include the flexible tube 72 that extends from the pump device 100 to the subcutaneous cannula 76 retained by a skin adhesive patch 78 that secures the subcutaneous cannula 76 to the infusion site. The skin adhesive patch 78 can retain the infusion cannula 76 in fluid communication with the tissue or vasculature of the patient so that the medicine dispensed through the tube 72 passes through the cannula 76 and into the user's body. The cap device 130 may provide fluid communication between the output end 122 (FIG. 2) of the medicine cartridge 120 and the tube 72 of the infusion set 70. For example, the tube 72 may be directly connected to the output port 139 (FIG. 2) of the cap device 130. In another example, the infusion set 70 may include a connector (e.g., a Luer connector or the like) attached to the tube 72, and the connector can then mate with the cap device 130 to provide the fluid communication to the tube 72. In these examples, the user can carry the portable infusion pump assembly 60 (e.g., in the user's pocket, connected to a belt clip, adhered to the user's skin, or the like) while the tube 72 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module.

Referring to FIG. 3, in some embodiments, the infusion pump assembly 60 is pocket-sized so that the pump device 100 and controller device 200 can be worn in the user's pocket 6 or in another portion of the user's clothing. For example, the pump device 100 and the controller device 200 can be attached together and form the assembly 60 that comfortably fits into a user's pocket 6. The user can carry the portable infusion pump assembly 60 and use the tube 72 of the infusion set 70 to direct the dispensed medicine to the desired infusion site. In some circumstances, the user may desire to wear the pump assembly 60 in a more discrete manner. Accordingly, the user may pass the tube 72 from the pocket 6, under the user's clothing, and to the infusion site where the adhesive patch 78 is positioned. As such, the pump system 10 can be used to deliver medicine to the tissues or vasculature of the user in a portable, concealable, and discrete manner. Furthermore, the monitoring device 50 can be worn on the user's skin while the pump assembly 60 is carried by the user (e.g., in a pocket). As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

Referring to FIG. 4, in other embodiments, the infusion pump assembly 60 may be configured to adhere to the user's skin 7 directly at the location in which the skin is penetrated for medicine infusion. For example, a rear surface of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula 76 that is penetrated into the user's skin. In one example, the fluid output port 139 through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220. Furthermore, the monitoring device 50 can be worn on the user's skin while the pump assembly 60 is worn on the user's skin in a different location from that where the monitoring device is worn. As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

In the embodiments depicted in FIGS. 3-4, the monitoring device 50 adheres to the user's skin 7 at the location in which the skin is penetrated by the sensor shaft 56 (to detect blood glucose levels). The sensor shaft 56 (refer to FIG. 1) penetrates the skin surface for the purpose of exposing the tip portion of the sensor shaft 56 to the tissue or the vasculature of the user. The sensor shaft 56 can detect information indicative of the user's blood glucose level and transfer this information to a circuit that is connected to the communications device 54 located within the monitoring device 50. The communication device 54 can be in wireless communication with the communication device 247 (described in connection with FIG. 9) included in the controller device 200 of the pump assembly 60.

Referring now to FIGS. 5-8, in some embodiments, the infusion pump assembly 60 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 may be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, in some embodiments, the medicine cartridge 120 containing insulin may have an expected usage life about 7 days after the cartridge is removed from a refrigerated state and the septum 121 (FIG. 2) is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin may become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 may be designed to have an expected operational life of about 1 year to about 7 years, about 2 years to about 6 years, or about 3 years to about 5 years—depending on a number of factors including the usage conditions for the individual user. Accordingly, the user is permitted to reuse the controller device 200 (which may include complex or valuable electronics) while disposing of the relatively low-cost pump device 100 after each use. Such a pump system 10 can provide enhanced user safety as a new pump device 100' (and drive system therein) is employed with each new fluid cartridge 120.

Referring to FIGS. 5-6, the pump device 100 can be readily removed from the controller device 200 when the medicine cartridge 120 is exhausted. As previously described, the medicine cartridge 120 is arranged in the cavity 116 (FIG. 2) of the pump housing 110 where it is retained by the cap device 130. In some embodiments, a portion of the pump housing 110 can comprise a transparent or translucent material so that at least a portion of the medicine cartridge 120 is viewable therethrough. For example, the user may want to visually inspect the medicine cartridge when the plunger 125 is approaching the output end 122 of the medicine cartridge, thereby providing a visual indication that the medicine cartridge may be emptied in the near future. In this embodiment, the barrel 111 of the pump housing 110 comprises a generally transparent polymer material so that the user can view the medicine cartridge 120 to determine if the plunger 125 is nearing the end of its travel length.

As shown in FIG. 5, the pump device 100 has been used to a point at which the medicine cartridge 120 is exhausted. The plunger 125 has been advanced, toward the left in FIG. 5, over a period of time so that all or most of the medicine has been dispensed from the cartridge 120. In some embodiments, the controller device 200 may provide a visual or audible alert when this occurs so as to remind the user that a new medicine cartridge is needed. In addition or in the alternative, the user may visually inspect the medicine cartridge 120 through the barrel 111 of the pump housing 110 to determine if the medicine cartridge 120 is almost empty. When the user determines that a new medicine cartridge 120 should be employed, the pump device 100 can be readily separated from the controller device 200 by actuating a release member 215. In this embodiment, the release member 215 is a latch on the controller device 200 that is biased toward a locking position to engage the pump device 100. The latch may be arranged to engage one or more features on a lateral side of the pump housing 110. As such, the user may actuate the release member 215 by moving the release member 215 in a lateral direction 216 (FIG. 5) away from the pump device 100 (e.g., by applying a force with the user's finger).

As shown in FIG. 6, when the release member 215 is actuated and moved to a position away from the pump device 100, a segmented guide rail 114a-b is free to slide longitudinally in a guide channel 214a-b without interference from the release member 215. Accordingly, the user can move the pump device 100 in a longitudinal direction 217 away from the controller device 200. For example, the segmented guide rail 114a-b may slide along the guide channel 214a-b, the extension 113 (FIG. 2) may be withdrawn from the mating depression 213 (FIG. 6), and the electrical connector 118 can be separated from the mating connector 218. In these circumstances, the pump device 100 is physically and electrically disconnected from the controller device 200 while the pump device retains the exhausted medicine cartridge 120. It should be understood that, in other embodiments, other features or connector devices can be used to facilitate the side-by-side mounting arrangement. These other features or connector devices may include, for example, magnetic attachment devices, mating tongues and grooves, or the like.

In some embodiments, the gasket 140 compressed between the pump device 100 and the controller device 200 may comprise a resilient material. In such circumstances, the gasket 140 can provide a spring-action that urges the pump device 100 to shift a small amount away from the controller device 200 when the release member 215 is moved to the unlocked position (e.g., moved in the lateral direction 216 in the embodiment shown in FIG. 5). Accordingly, in some embodiments, the pump device 100 can automatically and sharply move a small distance (e.g., about 0.5 mm to about 5 mm) away from the controller device 200 when the release member 215 is moved to the unlocked position. Such an automatic separation provides a convenient start for the user to detach the pump device 100 away from the controller device 200. Furthermore, this automatic separation caused by the spring-action of the gasket 140 can provide a swift disconnect between the electrical connectors 118 and 218 when the pump device 100 is being replaced.

Figure 7:
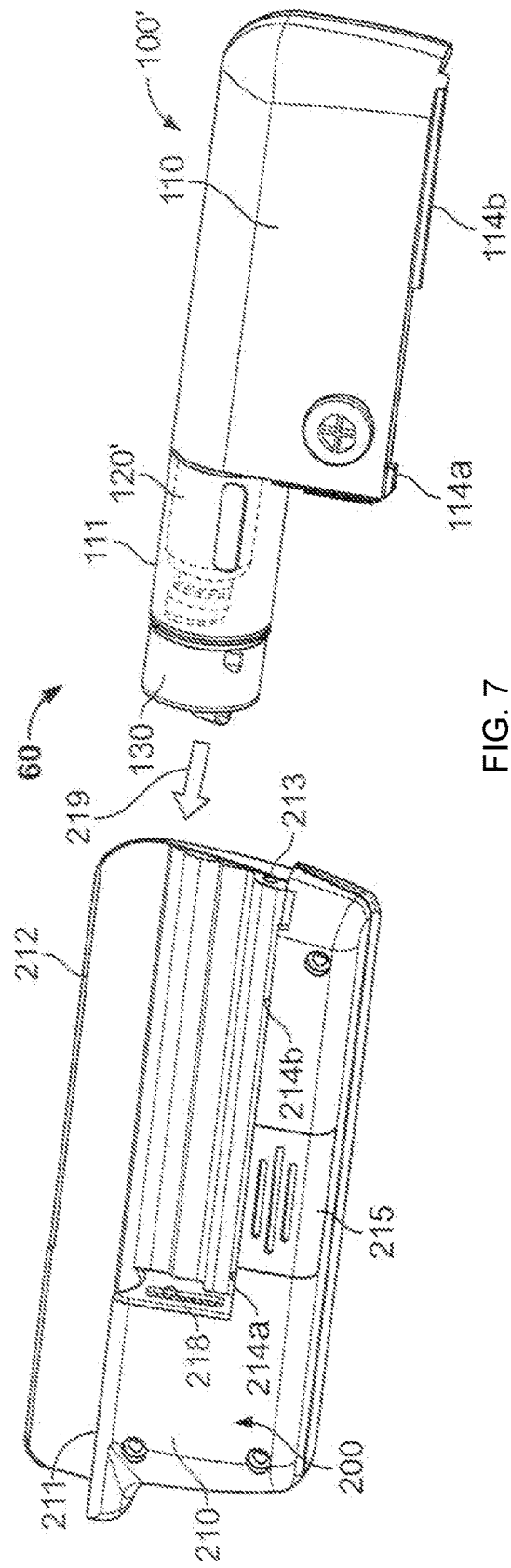
FIGS. 7-8 are perspective views of the pump device of FIGS. 5-6 being discarded and the controller device of FIGS. 5-6 being reused with a new pump device.
Figure 8:
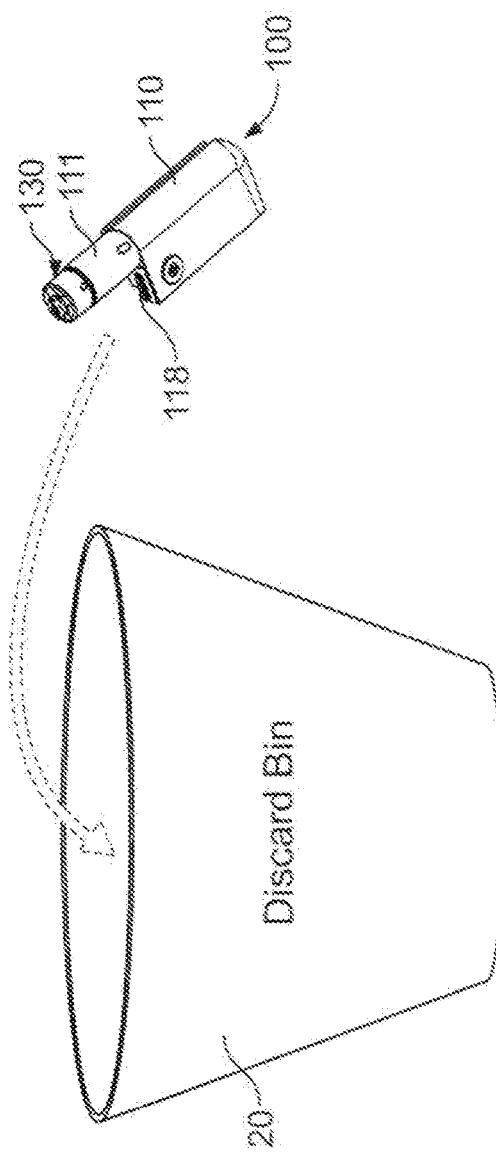

Referring to FIGS. 7-8, the same controller device 200 can be reused with a new pump device 100' having a new medicine cartridge 120' retained therein, and the previously used pump device 100 can be discarded with the exhausted medicine cartridge 120. The new pump device 100' (FIG. 7) can have a similar appearance, form factor, and operation as the previously used pump device 100 (FIGS. 5-6), and thus the new pump device 100' can be readily attached to the controller device 200 for controlled dispensation of medicine from the new medicine cartridge 120'. In some embodiments, the user may prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 2). Although the tubing 72 of the infusion set 70 is not shown in FIG. 7, it should be understood that the tubing 72 may be attached to the cap device 130 prior to the cap device 130 being joined with the housing 110. For example, a new infusion set 70 can be connected to the cap device 130 so that the tubing 72 can be primed (e.g., a selected function of the pump device 100 controlled by the controller device 200) before attaching the infusion set patch to the user's skin. As shown in FIG. 7, the new medicine cartridge 120' may be filled with medicine such that the plunger 125 is not viewable through the barrel 111. In some embodiments, the user can removably attach the pump device 100 to the controller device 200 by moving the pump device 100 in a longitudinal direction 219 toward the controller device 200 such that the segmented guide rail 114a-b engages and slides within the guide channel 214a-b. When the electrical connectors 118 and 218 mate with one another, the release member 215 can engage the segmented guide rails 114a-b to retain the pump device 100 with the controller device 200.

As shown in FIG. 8, the previously used pump device 100 that was separated from the controller device (as described in connection with FIGS. 5-6) may be discarded after a single use. In these circumstances, the pump device 100 may be configured as a disposable "one-time-use" device that is discarded by the user after the medicine cartridge 120 is emptied, is expired, has ended its useful life, or is otherwise exhausted. For example, the pump device 100 may be discarded into a bin 30, which may include a trash bin or a bin specifically designated for discarded medical products. Thus, the user is permitted to dispose of the relatively low-cost pump device 100 after each use while reusing the controller device 200 (which may include complex or valuable electronics) with subsequent new pumps 100'. Also, in some circumstances, the infusion set 70 (not shown in FIG. 8, refer to FIG. 1) that was used with the pump device 100 may be removed from the user and discarded into the bin 30 along with the pump device 100. Alternatively, the infusion set 70 can be disconnected from the previous pump device 100 and attached to the new pump device 100'. In these circumstances, the user may detach the infusion set cannula 76 and patch 78 from the skin so as to "re-prime" the tubing with medicine from the new pump device 100' to remove air pockets from the tubing. Thereafter, the infusion set cannula 76 and patch 78 can be again secured to the user's skin.

Figure 9:
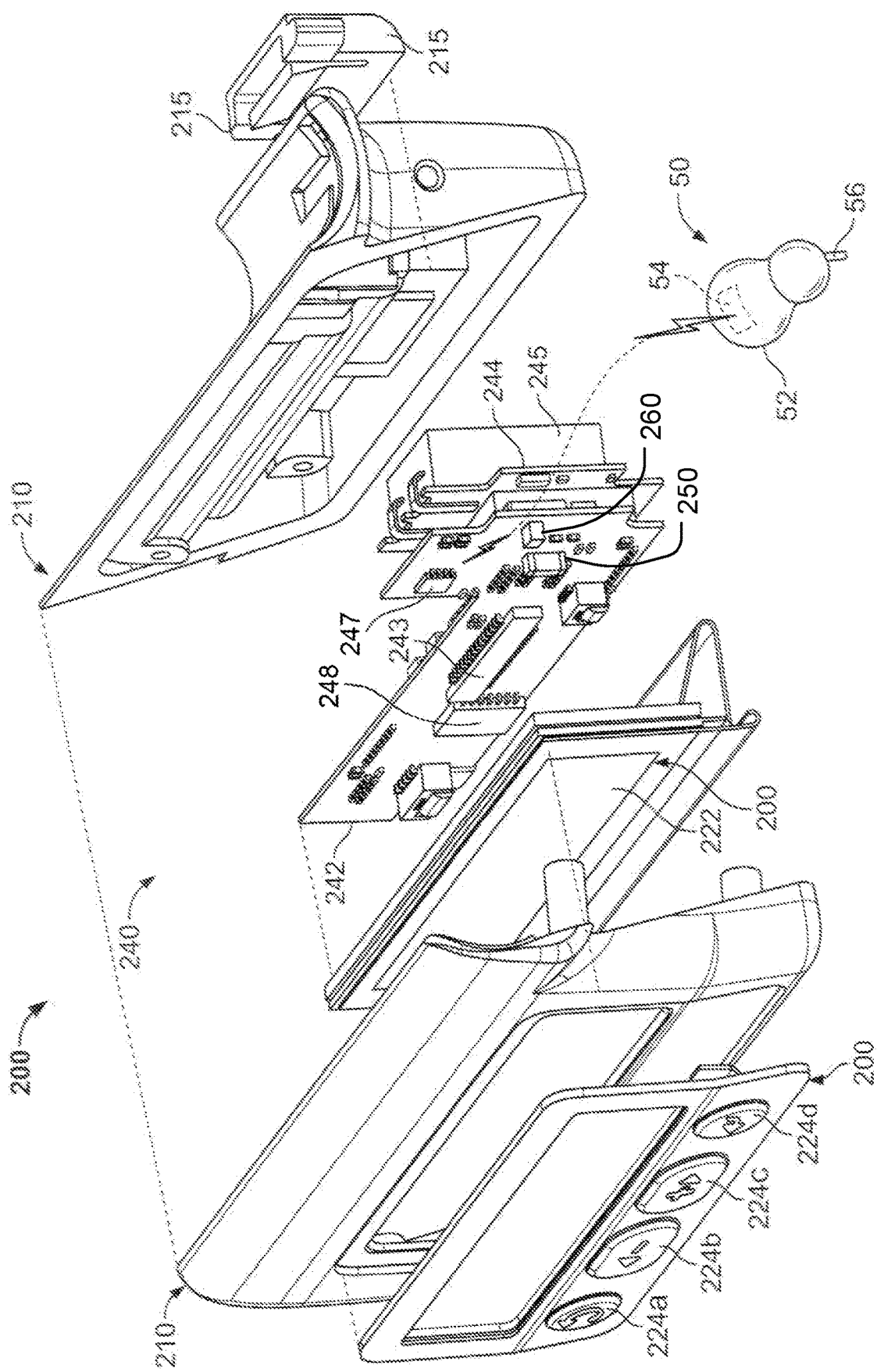
FIG. 9 is an exploded perspective view of a controller device for an infusion pump system, in accordance with some embodiments.

Referring now to FIG. 9, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100. In this embodiment, the control circuitry 240 includes a main processor board 242 that is in communication with a power supply board 244. The control circuitry 240 includes at least one processor 243 that coordinates the electrical communication to and from the controller device 200 (e.g., communication between the controller device 200 and the pump device 100). The processor 243 can be arranged on the main processor board 242 along with a number of other electrical components such as memory devices (e.g., memory chip 248). It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable in that the user may provide one or more instructions to adjust a number of settings for the operation of the infusion pump system 10. Such settings may be stored in the one or more memory devices, such as the memory chip 248 on the processor board 242. The control circuitry 240 may include other components, such as sensors (e.g., occlusion sensors, ambient air pressure sensors, temperature sensors), that are electrically connected to the main processor board 242. For example, in some embodiments the processor board 242 includes the ambient air pressure sensor 250 (e.g., barometric sensor, altimeter, GPS, potentiometric sensor, capacitive sensor, piezoelectric sensor, strain gauge sensor, etc.) and/or the temperature sensor 260 (e.g., thermistor, thermocouple, resistance temperature detector, etc.). In some embodiments, such sensors are mounted directly on the processor board 242. In other embodiments, such sensors are mounted on one or more auxiliary circuit boards that are in electrical communication with the processor board 242. In further embodiments, such sensors are remotely located from the processor board 242 and are in communication with the processor board 242 by hard-wiring. In alternative embodiments, such sensors are remotely located from the processor board 242 and are in communication with the processor board 242 by wireless communication (e.g., RF, infrared, Bluetooth, etc.). In some embodiments, such sensors may be located within the housings of the pump device 100 or the controller device 200. In other embodiments, such sensors may be located outside of the housings of the pump device 100 or the controller device 200. Furthermore, the control circuitry 240 may include one or more dedicated memory devices that store executable software instructions for the processor 243. The one or more memory devices (e.g., the memory chip 248) can also store information related to a user's blood glucose level and total insulin load (described in more detail in association with FIGS. 11-16B) over a period of time.

As previously described, the controller device 200 can be electrically connected with the pump device 100 via mating connectors 118 and 218 so that the control circuitry 240 can communicate control signals to the pump device 100 and receive feedback signals from components housed in the pump device 100. In this embodiment, the electrical connector 118 (FIG. 2) on the pump device 100 is a z-axis connector, and the connector 218 (FIG. 6) on the controller device 200 is adapted to mate therewith. The electrical connector 218 on the controller device 200 is in communication with the control circuitry 240. As such, the processor 243 can operate according to software instructions stored in the memory device so as to send control signals to the pump device 100 via the connector 218.

Still referring to FIG. 9, the user interface 220 of the controller device 200 can include input components, output components, or both that are electrically connected to the control circuitry 240. For example, in this embodiment, the user interface 220 includes a display device 222 having an active area that outputs information to a user and four buttons 224a-d that receive input from the user. Here, the display 222 may be used to communicate a number of status indicators, settings, and/or menu options for the infusion pump system 10. In some embodiments, the control circuitry 240 may receive the input commands from the user's button selections and thereby cause the display device 222 to output a number of status indicators (e.g., if the pump system 10 is delivering insulin, if the user's blood glucose level is rising or falling, and the like), menus, and/or program screens that show particular settings and data (e.g., the user's blood glucose level, the user's insulin load, the user's TIL % value, or the like). As previously described, the controller circuit 240 can be programmable in that the input commands from the button selections can cause the controller circuit 240 to change any one of a number of settings for the infusion pump system 100.

Some embodiments of the control circuitry 240 may include a cable connector (e.g., a USB connection port, another data cable port, or a data cable connection via the electrical connection 218) that is accessible on an external portion of the controller housing 210. As such, a cable may be connected to the control circuitry 240 to upload data or program settings to the controller circuit or to download data from the control circuitry 240. For example, historical data of blood glucose level, blood glucose alarm limits (including notification alert limits and safety alarm limits), medicine delivery (including basal and bolus deliveries), and/or TIL information can be downloaded from the control circuitry 240 (via the cable connector) to a computer system of a physician or a user for purposes of analysis and program adjustments. Optionally, the data cable may also provide recharging power.

Figure 10:
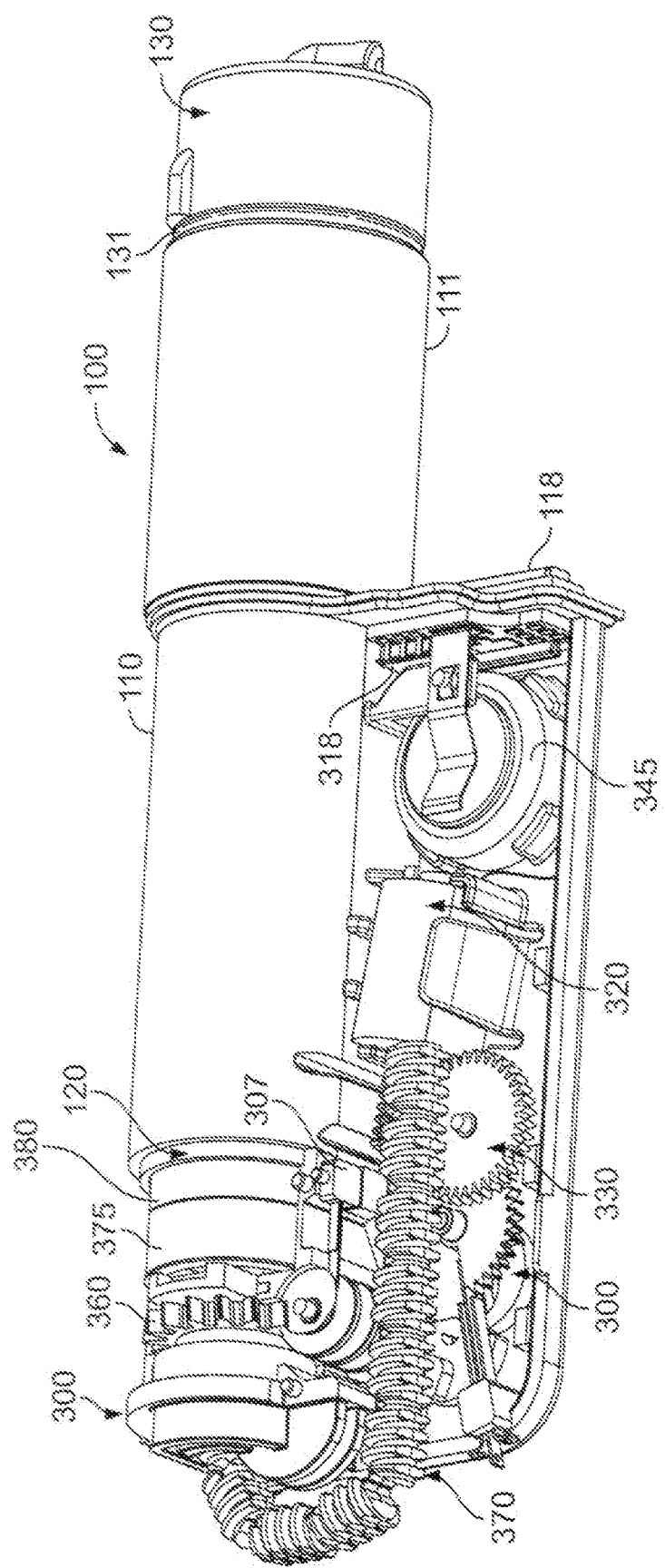
FIG. 10 is a perspective view of a portion of a pump device for an infusion pump system, in accordance with particular embodiments.

Referring to FIGS. 9-10, the control circuitry 240 of the controller device 200 may include a second power source 245 (FIG. 9) that can receive electrical energy from a first power source 345 (FIG. 10) housed in the pump device 100. In this embodiment, the second power source 245 is coupled to the power supply board 244 of the control circuitry 240. The hard-wired transmission of the electrical energy can occur through the previously described connectors 118 and 218. In such circumstances, the first power source 345 may include a high density battery that is capable of providing a relatively large amount of electrical energy for its package size, while the second power source 245 may include a high current-output battery that is capable discharging a brief current burst to power the drive system 300 of the pump device 100. Accordingly, the first battery 345 disposed in the pump device 100 can be used to deliver electrical energy over time (e.g., "trickle charge") to the second battery 245 when the controller device 200 is removably attached to the pump device 100. For example, the first battery 345 may comprise a zinc-air cell battery. The zinc-air cell battery 345 may have a large volumetric energy density compared to some other battery types. Also, the zinc-air cell battery may have a long storage life, especially in those embodiments in which the battery is sealed (e.g., by a removable seal tab or the like) during storage and before activation.

The second battery 245 may include a high current-output device that is housed inside the controller housing 210. The second battery 245 can be charged over a period of time by the first battery 345 and then intermittently deliver bursts of high-current output to the drive system 300 over a brief moment of time. For example, the second battery 245 may comprise a lithium-polymer battery. The lithium-polymer battery 245 disposed in the controller device 200 may have an initial current output that is greater than the zinc-air cell battery 345 disposed in the pump device 100, but zinc-air cell battery 345 may have an energy density that is greater than the lithium-polymer battery 245. In addition, the lithium-polymer battery 245 is readily rechargeable, which permits the zinc-air battery 345 disposed in the pump device 100 to provide electrical energy to the lithium-polymer battery 245 for purposes of recharging. In alternative embodiments, it should be understood that the second power source 245 may comprise a capacitor device capable of being recharged over time and intermittently discharging a current burst to activate the drive system 105.

Accordingly, the infusion pump system 10 having two power sources 345 and 245—one arranged in the pump device 100 and another arranged in the reusable controller device 200—permits a user to continually operate the controller device 200 without having to recharge a battery via an outlet plug-in or other power cable. Because the controller device 200 can be reusable with a number of pump devices 100 (e.g., attach the new pump device 100' after the previous pump device 100 is expended and disposed), the second power source 245 in the controller device can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing or possibly eliminating the need for separate recharging of the controller device 200 via a power cord plugged into a wall outlet.

Referring now to FIG. 10, the pump device 100 in this embodiment includes the drive system 300 that is controlled by the removable controller device 200 (see FIG. 2). Accordingly, the drive system 300 can accurately and incrementally dispense fluid from the pump device 100 in a controlled manner. The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. Some embodiments of the drive system 300 may include a battery powered actuator (e.g., reversible motor 320 or the like) that actuates a gear system 330 to reset a ratchet mechanism (e.g., including a ratchet wheel and pawl), a spring device (not shown) that provides the driving force to incrementally advance the ratchet mechanism, and a drive wheel 360 that is rotated by the ratchet mechanism to advance the flexible piston rod 370 toward the medicine cartridge 120. Connected to piston rod 370 is a pusher disc 375 for moving the plunger 125 of the medicine cartridge 120.

Some embodiments of the drive system 300 can include a pressure sensor 380 disposed between the plunger engagement device 375 and the plunger 125 for determining the pressure within the fluid path (e.g., inside the medicine cartridge 120, the infusion set 70, and the like). For example, the fluid pressure in the medicine cartridge 120 can act upon the plunger 125, which in turn can act upon the pressure sensor 380 arranged on the dry side of the plunger 125. The pressure sensor 380 may comprise a pressure transducer that is electrically connected (via one or more wires) to a gateway circuit 318 so that the sensor signals can be communicated to the controller device 200 (e.g., via the electrical connectors 118 and 218). As such, data from the pressure sensor 380 can be received by the controller device 200 for use with, for example, an occlusion detection module to determine if an occlusion exists in the medicine flow path. Alternatively, the controller device 200 may include an optical sensor system (not shown in FIGS. 9-10) to detect occlusions in the fluid path. For example, a light emitter and light sensor may each be arranged on a sensor circuit in the controller device 200 (but aligned with the pump device 100) so that the light sensor can detect the amount of light emitted by the light emitter and subsequently reflected from a component adjacent the fluid path. The reflected light level detected may be used to determine the pressure within the fluid path.

Referring now to FIG. 11, some embodiments of a portable infusion pump system 500 employing one or more of the aforementioned features for detecting and responding to ambient air pressure and temperature conditions (e.g., similar to those depicted in any of FIGS. 1, 2, and 9) can include a reusable pump apparatus (rather than a disposable pump device as previously described). In such circumstances, the infusion pump system 500 may comprise a reusable device that houses the control circuitry and the pump drive system within a single housing construct. In the particular embodiment depicted in FIG. 11, the pump system 500 comprises a reusable pump device that houses both the control circuitry and the pump drive system (which may include a piston rod and one or more gears). Similar to previously described embodiments, the pump system 500 can include a housing structure that defines a cavity in which a medicine cartridge can be received (not shown in FIG. 11; refer for example to cartridge 120 in FIG. 2). For example, the pump system 500 can be adapted to receive a medicine cartridge in the form of a carpule that is preloaded with insulin or another medicine. The pump drive system can act upon the fluid cartridge to controllably dispense medicine through an infusion set 146 and into the user's tissue or vasculature. In this embodiment, the user can wear the portable pump system 500 on the user's skin under clothing or in the user's pocket while receiving the medicine dispensed through the infusion set 146.

The pump system 500 can also communicate with the aforementioned glucose monitoring device 50 for the purpose of receiving data indicative of a user's blood glucose level. Similar to previously described embodiments, the pump system 500 can utilize the data indicative of a user's blood glucose level to, for example, provide an alarm (e.g., an audible or textual safety alarm, an audible or textual alert notification, or another type of alarm) when the user's blood glucose level falls below a low glucose alarm limit or rises above a high glucose alarm limit.

In some embodiments, as described further below in connection with FIGS. 12 and 13, the infusion pump system 500 can monitor actual ambient conditions such as air pressure and temperature. In some such embodiments, the infusion pump system 500 can include an air pressure sensor 550 and/or a temperature sensor 560 that can measure the ambient pressure and temperature conditions respectively. The pressure sensor 550 and temperature sensor 560 can be in electrical communication with the control circuitry. The control circuitry can initiate an alarm (e.g., an audible or textual safety alarm, an audible or textual alert notification, or another type of alarm) when the measured ambient conditions exceed predetermined alarm limits. In some embodiments, such textual alarms or alerts can be displayed to the user on a display 522. In addition to alarming, in some embodiments the control circuitry via display 522 can provide instructions for the user to take actions to counteract the potential effects that the ambient conditions may potentially have on the infusion pump system 500. By implementing the instructions, the user's blood glucose level can be maintained within a desired range despite the exposure of the infusion pump system 10 to deviations in ambient conditions.

In some embodiments, the display 522 can indicate an alarm indicative of a high or low ambient air pressure status, a high or low temperature status, an indication that the pressure or temperature levels are rising or falling (e.g., a noteworthy change in pressure or temperature), an indication of a high or low blood glucose level status, and the like. In the example depicted in FIG. 11, the display 522 indicates an alert in which the control circuitry has sensed a high temperature condition (above a predetermined high threshold level). In this embodiment, the display 522 also prompts the user to take particular countermeasures (as described further in reference to FIGS. 12 and 13), such as replacing the medicine in the cartridge, thereby helping the user to maintain blood glucose levels within the normal range.

Still referring to FIG. 11, similar to previously described embodiments, the display device 522 can be used to communicate a number of settings or menu options for the infusion pump system 500. For example, the display device 522 can be used to communicate medicinal delivery information, such as the basal delivery rate, a bolus dosage, a historical record of medicine delivered, the amount of medicine remaining in the cartridge, or the like. In another example, the display device 522 can be used to communicate time and date information, which can be used by the user to determine dosage schedules, bolus delivery times, meal times, or the like. In such circumstances, the user may press one or more of the buttons 524a, 524b, 524c, 524d, and 524e to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). Also, the user can adjust the settings or otherwise program the pump system 500 by pressing one or more buttons 524a, 524b, 524c, 524d, and 524e of the user interface 520. Thus, the user can contemporaneously monitor the operation of the pump system 500, including any messages pertaining to actual ambient conditions such as air pressure and temperature that have exceeded threshold limit values.

Figure 12:
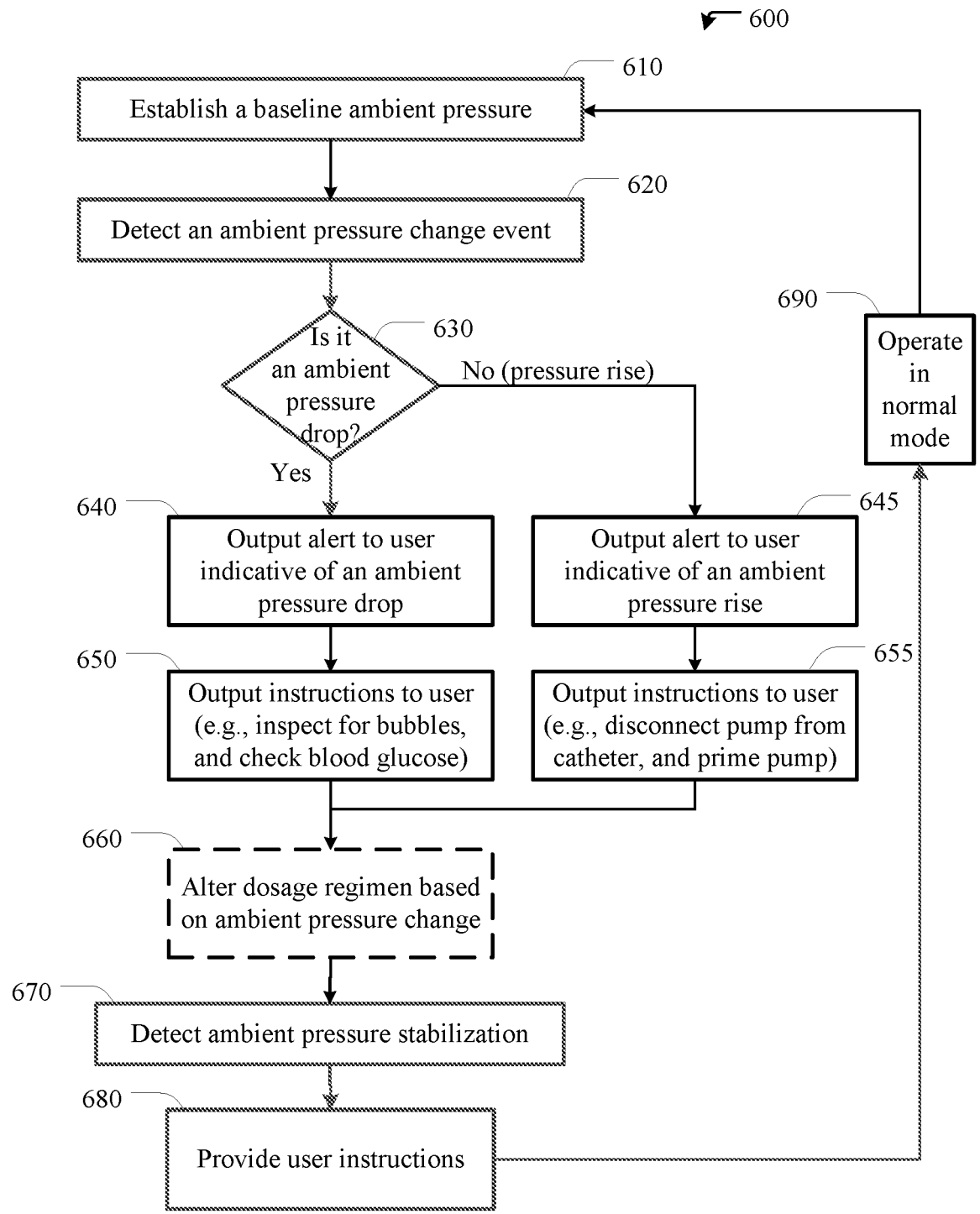
FIG. 12 is a flow diagram depicting an exemplary process for monitoring ambient air pressure and responding to alarm conditions, in accordance with some embodiments.
Figure 13:
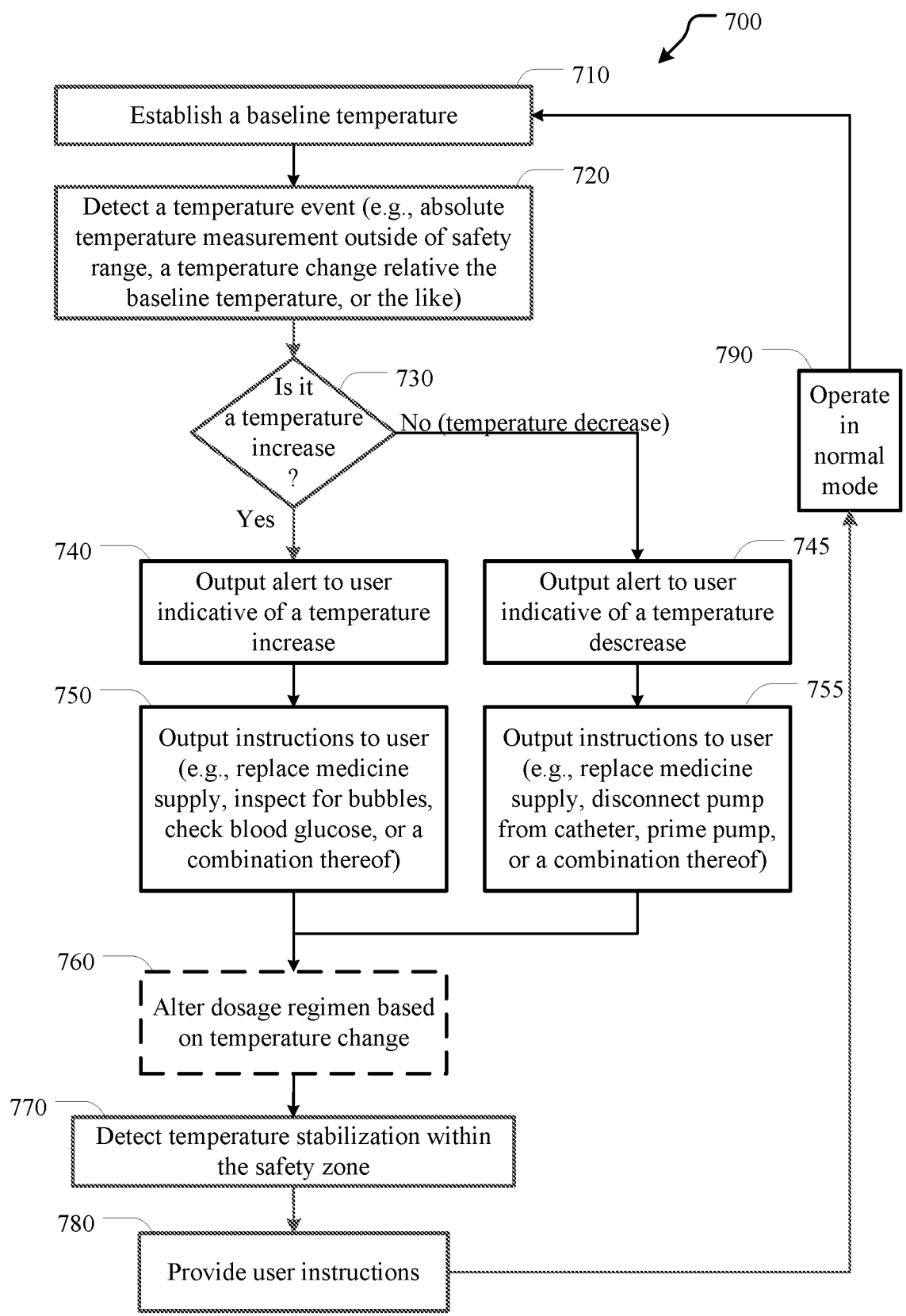
FIG. 13 is a flow diagram depicting an exemplary process for monitoring ambient air temperature and responding to alarm conditions, in accordance with some embodiments.

Referring now to FIGS. 12 and 13, which illustrate example methods whereby an infusion pump system can detect ambient events and alert the user to take preventive or corrective actions directed to, for example, maintaining the efficacy of the treatment provided by the infusion pump system. The example methods of FIGS. 12 and 13 will be described in the context of the example infusion pump system 10 (e.g., of FIGS. 1-10), however it should be understood from the description herein that the example methods can be implemented by other infusion pump systems, including but not limited to the infusion pump system 500 depicted in FIG. 11.

Referring to FIG. 12, a method 600 is depicted whereby infusion pump system can detect and respond to an ambient pressure change event. An ambient pressure change event may occur in various real-world scenarios, e.g., when the user of the infusion pump system flies on an airplane, when a significant weather/barometric change occurs, or the like. For example, in the airplane scenario, the ambient air pressure will tend to decrease as the airplane gains altitude, and the ambient air pressure will tend to increase as the airplane descends in altitude.

The method 600 may include operation 610, in which a baseline ambient air pressure is established. In some implementations, the baseline ambient air pressure can be the initial air pressure measured by the pressure sensor 250 at the time that the medicine cartridge 120 is installed into the pump device 100, and the pump device 100 is coupled to the controller device 200. In some implementations, the baseline ambient air pressure can be a long-term rolling average of measured air pressure values. For example, the controller device 200 may read a pressure value from the pressure sensor 250 on a periodic basis (e.g., every 1 second, 5 seconds, 10 seconds, 20 seconds, 30 seconds, 1 minute, 15 minutes or another appropriate time frequency) and store the value in memory (e.g., the memory chip 248). Then the processor 243 may calculate an average of the stored pressure values over a relatively long-term period of time (e.g., the past 12 hours, 1 day, 2 days, 3 days, 4 days or more). In some implementations, the calculated average can be established as the baseline ambient pressure.

At operation 620, the infusion pump system 10 can detect an ambient pressure change event (as defined further below). As described above, the pressure sensor 250 in conjunction with the controller device 200 can measure the ambient air pressure around the infusion pump system 10. The measured air pressure values can be compared to threshold limit values that have been programmed and stored in the controller device 200. If the measured air pressure values are outside of the threshold limit values an ambient pressure change event may have occurred. In some cases, signal conditioning (using hardware, software, or both) can be used to increase the confidence that an ambient pressure change event has occurred (e.g., to de-bounce the measured pressure values).

The pressure threshold limit values can be programmed and stored in the controller device 200. In some embodiments, the pressure threshold limit values are programmable by the user. In some embodiments, the threshold limit values are programmable only by an administrator of the infusion pump system 10, such as a physician, nurse, technician, or manufacturer. In some embodiments, the threshold limit values are programmable only using a computer system operated by an administrator of the infusion pump system 10, such as a physician, nurse, technician, or manufacturer.

In some embodiments, one or more types of ambient air pressure threshold limits can be established. For example, instantaneous air pressure threshold limit values can be established. In other words, if a measured air pressure value is outside of the acceptable range as defined within the boundaries of the instantaneous air pressure threshold limit values (upper and lower values), an ambient pressure change event can be deemed to have occurred. In another example, a pressure-change-over-time threshold limit value can be established. In other words, if successively measured air pressure values indicate that the air pressure is changing (upward or downward) more rapidly than the pressure-change-over-time threshold limit value, then an ambient pressure change event can be deemed to have occurred. In some embodiments, other types of ambient air pressure threshold limits can also be established.

At operation 630, in response to the detection of an ambient pressure change event from operation 620, the infusion pump system 10 determines whether the ambient pressure change event was an ambient pressure increase or decrease (e.g., relative to the baseline ambient pressure). If the ambient pressure change event was an ambient pressure increase (e.g., a pressure rise), the process proceeds to operation 645. If the ambient pressure change event was an ambient pressure decrease (e.g., a pressure drop), the process proceeds to operation 640.

In the event of a detected pressure drop beyond the threshold limit, the method continues to operation 640, in which the controller device 200 can output an alert indicative of an ambient pressure decrease. For example, in some embodiments the controller device 200 can output an audible or textual safety alarm, an audible or textual alert notification, a vibrating alarm, a LED light alarm, another communicative alarm output, or combinations thereof.

In some embodiments, the ambient condition alert feature of operation 640 can be user-selectable. That is, in some embodiments the user can select options to activate or deactivate some types or all types of the ambient event alert messages. For example, in some cases the user may desire to activate the pressure change alert message feature, but to deactivate the temperature change alert message feature. Or, in some cases the user may desire to deactivate the pressure change alert message feature, but to activate the temperature change alert message feature. Or, in some cases the user may desire to activate both the pressure change alert message feature and the temperature change alert message feature. Or, in some cases the user may desire to deactivate both the pressure change alert message feature and the temperature change alert message feature.

In some embodiments, the user may be provided with the option to "snooze" the ambient event alert for example, while he or she is taking actions to resolve the alarm circumstances. For example, the user interface can display a "snooze" or "postpone" option, which can be selected by the user to silence the alarm for a predetermined period of time (e.g., 5 minutes, 10 minutes, 15 minutes, 1 hour, or the like). In some embodiments, the settings that control the duration of the "snooze" timer can be modified to reduce the occurrences of repeated nuisance alarms or to increase the occurrence of alarms when the ambient conditions are far outside the alarm limits.

At operation 650, the controller device 200 can output instructions to the user using the display 222 (e.g., refer to FIG. 1). For example, in response to a detected ambient pressure drop the user may be provided with instructions to inspect the flexible tube 72 of the infusion set 70 to check if any bubbles are present. Bubbles may form in the fluid medicine in response to a significant pressure decrease because dissolved gasses in the medication liquid may tend to leave the liquid and form sizeable bubbles as the pressure decreases. Having bubbles in the liquid medicine can cause inaccurate dispensations of the medicine because as the bubbles form some medicine may be displaced into the user. If bubbles are present in the medicine, further pressure decreases can allow the bubbles to expand and thereby dispense additional medicine to the user unintentionally. In addition, bubbles can lead to later unintended under-delivery of medicine if the bubbles are delivered to the user in place of the medicine. If air bubbles are found in the flexible tube 72, the controller device 200 can output textual instructions that prompts the user to disconnect the flexible tube 72 from the user (e.g., removing the tube 72 from the cannula housing 74, removing the entire tube 72 and cannula housing 74 from the skin surface, or the like) and flush a portion of the fluid medicine from the infusion pump system 10 that through the tube 72 (e.g., similar to a priming operation) so as to remove the air bubbles. Alternatively, if air bubbles are found in the flexible tube 72, the controller device 200 can output textual instructions that prompts the user to disconnect the infusion set 70 and to replace it with a new infusion set 70 (e.g., connecting the new infusion set to the pump device 100.

In some embodiments, the controller device 200 user may also provide instructions that prompts the user to take a contemporaneous blood glucose measurement. For example, taking a blood glucose measurement may be advisable in light of the potential that the ambient air pressure decrease may have caused bubble formation in the medicine that resulted in unintended dispensation of medicine. In some embodiments of the infusion pump system 10 in which the controller device 200 is equipped with a blood strip reader, a test strip (e.g., blood test strip) containing a sample of the user's blood can be inserted into the strip reader portion of the controller device 200 for testing the user's blood glucose level and automatically inputting the value into the controller 200. Alternatively, the test strips (e.g., glucose test strips) containing a sample of the user's blood can be inserted into a separate glucose meter device (not shown), which can then analyze the characteristics of the user's blood and communicate the information (via a wired or wireless connection) to the controller device 200. In still other embodiments, characteristics of the user's blood glucose information can be measured by a separate glucose meter device (not shown) and then manually entered directly into controller device 200 via the user interface 220. Or, in some embodiments, the infusion pump system 10 (refer, for example, to FIG. 1) can include a glucose monitoring device such as glucose monitoring device 50. In some such embodiments, the glucose monitoring device 50 can be in communication with the pump assembly 60 via wireless communications or a wired connection. Using such example techniques, the user's blood glucose reading can be promptly measured in response to the ambient pressure drop alert.

Operations 640 and 650 pertaining to an ambient pressure drop having been described above, now the operations 645 and 655 pertaining to an ambient pressure increase will be described.

In the event of a detected pressure increase beyond the threshold limit, the method continues to operation 645, in which an alert that is indicative of an ambient pressure rise is provided to the user. For example, in some embodiments the controller device 200 can output an audible or textual safety alarm, an audible or textual alert notification, a vibrating alarm, a LED light alarm, another communicative alarm output, or combinations thereof. As described above in reference to operation 640, in some embodiments the alert can be user-selectable and the aforementioned snooze function may be provided.

At operation 655, the controller device 200 can output textual instructions to the user using the display 222. For example, in response to an ambient air pressure rise, the controller device 200 can output textual instructions that prompts the user to disconnect the flexible tube 72 from the user (e.g., removing the tube 72 from the cannula housing 74, removing the entire tube 72 and cannula housing 74 from the skin surface, or the like) and to prime a few units of medicine through the tube 72 so as to remove the air bubbles. Alternatively, if air bubbles are found in the flexible tube 72, the controller device 200 can output textual instructions that prompts the user to disconnect the entire infusion set 70 and to replace it with a new infusion set 70 (e.g., connecting the new infusion set to the pump device 100. These instructs to the user may be warranted because a significant ambient pressure rise can cause the volume of the flow path occupied by the medicine to decrease, thereby generating some empty space within the flexible tube 72 (which could lead to an under-delivery of medicine if not remedied).

Optionally, the method 600 can also include operation 660, in which the infusion pump system 10 alters the medicine dosage regimen based on the ambient pressure change. In some embodiments, in addition to alerting the user about the changes in ambient conditions, the infusion pump system 10 can alter the delivery of medicine in attempt to compensate of a projected change in delivery due to the change in ambient air pressure. This could be done to compensate for any known trapped air within the medicine path (such as a small volume of air trapped in the occlusion detector of the infusion pump system 10) or to compensate for a projected amount of bubble formation and growth based on typical medications and environmental conditions. When a pressure change is detected, the infusion pump system 10 can, in some embodiments, alter previously programmed dispensations of medicine in proportion with the change in pressure. In some cases, for an increase in pressure, the delivery would be increased. In some cases, for a decrease in pressure, the deliveries would be decreased.

Still referring to FIG. 12, the method 600 may include operation 670, in which the infusion pump system detects that the ambient pressure has stabilized for a period of time. The detection is made by pressure sensor 250 in conjunction with controller device 200. In response to the detected stabilization of the ambient pressure, the process proceeds to operation 680.

At operation 680, the infusion pump system 10 provides the user with additional textual instructions via the user interface 220. For example, when the pressure has stabilized, the controller device 200 can output textual instructions that prompts the user to check for bubbles and to remove them by flushing. In addition, the controller device 200 can output textual instructions that prompts the user to monitor health symptoms, and to measure blood glucose. In general, the instructions may be directed to re-establishing normal operations of the infusion pump system 10.

At operation 690, the infusion pump system 10 resumes normal operations. After resuming normal operations, the process 600 returns to operation 610 where a new baseline ambient pressure is determined based on measurements of the ambient air pressure by pressure sensor 250 in conjunction with controller device 200.

Referring now to FIG. 13, a method 700 is depicted whereby infusion pump system can detect and respond to an ambient temperature event. A temperature event may occur in various real-world scenarios, e.g., when the user of the infusion pump system 10 goes outdoors into a very warm or a very cold climate, when a user enters a sauna or steam bath, or the like. As previously described, the example method depicted in FIG. 13 will be described in the context of the example infusion pump system 10 (e.g., of FIGS. 1-10), however it should be understood from the description herein that the example method can be implemented by other infusion pump systems, including but not limited to the infusion pump system 500 depicted in FIG. 11.

The method 700 may include operation 710, in which a baseline ambient temperature is established. In some implementations, the baseline ambient temperature will be established by default at room temperature (about 19 degrees Celsius to about 25 degrees Celsius, and about 20 degrees Celsius in this particular example). In some implementations, the baseline ambient temperature will be a long-term rolling average of measured temperature values. For example, the controller device 200 may determine a temperature value from the temperature sensor 260 on a periodic basis (e.g., every 1 second, 5 seconds, 10 seconds, 20 seconds, 30 seconds, 1 minute, 15 minutes or another appropriate time frequency) and store the value in memory (e.g., the memory chip 248). Then the processor 243 may calculate an average of the stored temperature values over a relatively long-term period of time (e.g., the past 12 hours, 1 day, 2 days, 3 days, 4 days or more). In some implementations, the calculated average can be established as the baseline temperature.

At operation 720, the infusion pump system 10 can detect a temperature event (e.g., an absolute temperature measurement outside of a predetermined range, a temperature change relative to the baseline temperature, or the like). As described above, in some embodiments the temperature sensor 260 in conjunction with the controller device 200 can measure the ambient temperature around the infusion pump system 10. In some embodiments, the processor 243 itself may have the capabilities to measure temperature. The measured temperature values can be compared to threshold limit values that have been programmed and stored in the controller device 200. If the measured temperature values are outside of the threshold limit values, a temperature event may have occurred. In some cases, signal conditioning (using hardware, software, or both) can be used to increase the confidence that a temperature event has occurred (e.g., to de-bounce the measured pressure values). In some cases, an offset adjustment can be applied to the measured temperature value to compensate for the conditions near the temperature sensor 260 (e.g., to better approximate the temperature of the medicine).

The temperature threshold limit values can be programmed and stored in the controller device 200. In some embodiments, the temperature threshold limit values are programmable by the user. In some embodiments, the threshold limit values are programmable only by an administrator of the infusion pump system 10, such as a physician, nurse, technician, or manufacturer. In some embodiments, the threshold limit values are programmable only using a computer system operated by an administrator of the infusion pump system 10, such as a physician, nurse, technician, or manufacturer.

In some embodiments, one or more types of ambient temperature threshold limits can be established. For example, instantaneous temperature threshold limit values can be established. In other words, if a measured temperature value is outside of the acceptable range as defined within the boundaries of the instantaneous temperature threshold limit values (upper and lower values), a temperature event can be deemed to have occurred. In some embodiments, various levels of instantaneous temperature threshold limit values can be established. For example, absolute threshold levels (e.g., a lower value of 0 degrees Celsius and an upper value of 40 degrees Celsius) can be established. If the instantaneous measured temperature value falls outside of this absolute threshold range (0 to 40 degrees Celsius in this example), the controller device 200 can out instructions via the user interface 220 that prompts the user to discard and replace the medicine supply (e.g., insulin cartridge in this embodiment). In another example, a temperature-change-over-time threshold limit value can be established. In other words, if successively measured temperature values indicate that the temperature is changing (upward or downward) more rapidly than the temperature-change-over-time threshold limit value (e.g., a significant temperature shock), then a temperature event can be deemed to have occurred. In some embodiments, other types of ambient temperature threshold limits can also be established.

At operation 730, in response to the detection of a temperature event from operation 720, the infusion pump system 10 determines whether the temperature event was a temperature increase or decrease. If the temperature event was a temperature decrease, the process proceeds to operation 745. If the temperature event was a temperature increase, the process proceeds to operation 740.

At operation 740, the controller device 200 can output an alert indicative of a temperature increase. For example, in some embodiments the controller device 200 can output an audible or textual safety alarm, an audible or textual alert notification, a vibrating alarm, a LED light alarm, another communicative alarm output, or combinations thereof.

As described above, in some embodiments the ambient condition alert feature of operation 740 can be user-selectable. That is, in some embodiments the user can select to activate or deactivate some types or all types of the ambient event alert messages. In addition, in some embodiments the user may be provided with the aforementioned option to "snooze" the ambient event alert, for example while the user is taking actions to resolve the alarm circumstances.

At operation 750, the controller device 200 can output instructions via the display 222 (e.g., refer to FIG. 1, or display 522 of FIG. 11) that prompts the user to take one or more corrective actions. For example, in response to a detected temperature increase the user may be provided with instructions to inspect the flexible tube 72 of the infusion set 70 to see if any bubbles are present. Bubbles may form in the medicine in response to a temperature increase because dissolved gasses in the medication liquid may tend to leave the liquid and form bubbles as the temperature increases. Having bubbles in the liquid medicine can cause inaccurate dispensations of the medicine because as the bubbles form some medicine may be displaced into the user. If bubbles are present in the medicine, further temperature increases can allow the bubbles to expand and thereby dispense additional medicine to the user unintentionally. In addition, bubbles can lead to later unintended under-delivery of medicine if the bubbles are delivered to the user in place of the medicine. If air bubbles are found in the flexible tube 72, in some embodiments the user can disconnect the flexible tube 72 from the cannula housing 74 and flush the infusion pump system 10 to remove the air bubbles.

In some cases, if the temperature detected is above an absolute threshold value (e.g., a high threshold value selected from a range of about 37 degrees Celsius to about 42 degrees Celsius, and about 40 degrees Celsius in this example), the controller device 200 can output instructions via the user interface 220 that prompts the user to discard the medicine supply. That is because, for example, insulin can deteriorate or otherwise lose some efficacy when exposed to temperatures substantially above human body temperature (about 37 degrees Celsius). In such a case, the infusion pump system 10 can provide instructions to discard the medicine. In some cases, the duration of time that the temperature was near or above the extreme threshold value can also be taken into account in regard to the provision of instructions. That is, the duration of time can be combined with the temperature (e.g., 43 degrees Celsius for a period of 10 minutes) in a formula that quantifies the potential for medicine degradation. In some cases, if the duration of time that the temperature was near or above the extreme threshold value was long enough, the infusion pump system 10 may self-disable the drive system so that no further dispensations of medicine are provided until the medicine cartridge 120 has been replaced.

In some embodiments, the controller device 200 can output instructions via the user interface 220 that prompts the user to take a blood glucose measurement. For example, taking a blood glucose measurement may be advisable in light of the potential that the temperature increase may have caused bubble formation in the medicine that resulted in unintended dispensation of medicine.

Operations 740 and 750 pertaining to a temperature increase having been described above, the operations 745 and 755 pertaining to a temperature decrease will now be described. At operation 745 an alert that is indicative of a temperature decrease event is provided to the user. For example, in some embodiments the controller device 200 can output an audible or textual safety alarm, an audible or textual alert notification, a vibrating alarm, a LED light alarm, another communicative alarm output, or combinations thereof. As described above in reference to operation 740, in some embodiments the alert can be user-selectable and the aforementioned snooze function may be provided.

At operation 755, the controller device 200 can output textual instructions to the user via the display 222. For example, in response to a temperature decrease, the controller device 200 can output instructions via the user interface 220 that prompts the user to disconnect the flexible tube 72 from the user (e.g., removing the tube 72 from the cannula housing 74, removing the entire tube 72 and cannula housing 74 from the skin surface, or the like) and to prime a few units of medicine through the tube 72 so as to remove the air bubbles. Alternatively, if air bubbles are found in the flexible tube 72, the controller device 200 can output textual instructions that prompts the user to disconnect the entire infusion set 70 and to replace it with a new infusion set 70 (e.g., connecting the new infusion set to the pump device 100. These instructs to the user may be warranted because, in response to a significant temperature drop, the volume of the medicine may have decreased leaving some empty space within the flexible tube 72 (which could lead to an under-delivery of medicine if not remedied).

In some cases, if the temperature detected is below an extreme threshold value (e.g., a high threshold value selected from a range of about −4 degrees Celsius to about 2 degrees Celsius, and about 0 degrees Celsius in this example), the controller device 200 can output instructions via the user interface 220 that prompts the user to discard the medicine. That is because, for example, insulin can deteriorate or otherwise lose some efficacy when exposed to freezing temperatures (about 0 degrees Celsius or less). In such a case, the controller device 200 can output instructions via the user interface 220 that prompts the user to discard the medicine supply. In some cases, the duration of time that the temperature was near or below the extreme threshold value can also be taken into account in regard to the provision of instructions. That is, the duration of time can be combined with the temperature (e.g., −5 degrees Celsius for a period of 8 minutes) in a formula that quantifies the potential for medicine degradation. In some cases, if the duration of time that the temperature was near or below the extreme threshold value was long enough, the infusion pump system 10 may self-disable the pump drive system to prevent further dispensations of medicine until the medicine cartridge 120 has been replaced.

At operation 760, the infusion pump system 10 can optionally alter the dosage regimen based on the temperature change. In some embodiments, in addition to alerting the user about the changes in ambient conditions, the infusion pump system 10 could alter the delivery of medicine in attempt to compensate of a projected change in delivery due to the change in temperature. This could be done to compensate for any known trapped air within the medicine path (such as a small volume of air trapped in the occlusion detector of the infusion pump system 10) or to compensate for a projected amount of bubble formation and growth based on typical medications and environmental conditions. When a temperature change is detected, the infusion pump system 10 can, in some embodiments, alter previously programmed dispensations of medicine in proportion with the change in temperature. In some cases, for a decrease in temperature, the delivery would be increased. In some cases, for an increase in temperature, the deliveries would be decreased.

At operation 770, the temperature is detected to be stable within ambient temperature threshold limits (e.g., greater than the low absolute limit of 0 degrees Celsius and lower than the high absolute limit of 40 degrees Celsius in this example). The detection is made by temperature sensor 260 in conjunction with controller device 200. In response to the detected stabilization of the temperature, the process proceeds to operation 780.

At operation 780, the infusion pump system 10 provides the user with instructions via display 222. For example, when the temperature has stabilized, in some embodiments the controller device 200 can output instructions via the user interface 220 that prompts the user to check for bubbles and remove them by flushing. In addition, the controller device 200 can output instructions via the user interface 220 that prompts the user to monitor health symptoms, and to measure blood glucose. In general, the instructions can be directed to re-establishing normal operations of the infusion pump system 10.

At operation 790, the infusion pump system 10 resumes normal operations. After resuming normal operations, the process 700 returns to operation 710 where a new baseline temperature is determined based on measurements of the ambient temperature by temperature sensor 260 in conjunction with controller device 200 (or, alternatively, based upon the predefined setting such as the standard room temperature).

A number of embodiments of the invention have been described. Nevertheless, it will be understood that various modifications may be made without departing from the spirit and scope of the invention. Accordingly, other embodiments are within the scope of the following claims.

What is claimed is:

1. A medical infusion pump system, comprising:
a portable pump housing that receives an insulin supply for dispensation to a user, the pump housing at least partially containing a pump drive system to dispense insulin from the insulin supply through a flow path to the user;
a controller that communicates with the pump drive system to dispense the insulin from the portable pump housing; and
an ambient pressure detection device that communicates with the controller,
a memory device storing computer executable instructions that, when executed by the controller, cause the controller to perform operations, the operations comprising:
receiving, by the controller and from the ambient pressure detection device, ambient air pressure information indicative of an ambient air pressure external of the medical infusion pump system;
determining if the ambient air pressure information is less than a low limit threshold value or greater than a high limit threshold value;
determining, after determining the ambient air pressure information is less than the low limit threshold value or greater than the high limit threshold value, that the ambient air pressure has stabilized for a pre-specified period of time;
in response to determining that the ambient air pressure has stabilized for the pre-specified period of time, outputting user instructions to inspect a flexible tube that makes up a part of the flow path for bubbles in the medical infusion pump system and to remove the bubbles by flushing.

2. The system of claim 1, the operations further comprising:
in response to determining that the ambient air pressure has stabilized for the pre-specified period of time, outputting additional user instructions to measure a blood glucose level for the user of the medical infusion pump system.

3. The system of claim 1, the operations further comprising:
resuming operation of the medical infusion pump system in response to a user input, and wherein the user input is received by the controller while the ambient air pressure information is indicating that the ambient air pressure is less than the low limit threshold value or greater than the high limit threshold value.

4. The system of claim 1, the operations further comprising:
in response to determining that the ambient air pressure has stabilized for the pre-specified period of time, outputting additional user instructions to replace a medicine cartridge of the medical infusion pump system.

5. The system of claim 1, wherein the low limit threshold value or the high limit threshold value is determined, at least in part, based on a first baseline ambient pressure value, the operations further comprising:
in response to determining that the ambient air pressure has stabilized for the pre-specified period of time, determining a second baseline ambient pressure based on additional ambient air pressure information indicative of the ambient air pressure external of the medical infusion pump system.

6. The system of claim 1, wherein the user instructions include instructions to disconnect the flexible tube and to flush a portion of the insulin contained by the medical infusion pump system through the flexible tube.

7. The system of claim 1, wherein the user instructions include instructions to a) disconnect the flexible tube from a cannula housing that includes a cannula attached to an underside of the cannula housing and configured to be secured to an infusion site, and b) to flush a portion of the insulin contained by the medical infusion pump system through the disconnected flexible tube.

8. The system of claim 1, wherein the user instructions include instructions to a) disconnect the flexible tube and a cannula housing that includes a cannula attached to an underside of the cannula housing from a skin surface, and b) to flush a portion of the insulin contained by the medical infusion pump system through the disconnected flexible tube.

9. A method of operating a medical infusion pump system, comprising:
a portable pump housing receiving an insulin supply for dispensation to a user, the pump housing at least partially containing a pump drive system to dispense insulin from the insulin supply through a flow path to the user;
a controller communicating with the pump drive system to dispense the insulin from the portable pump housing;
an ambient pressure detection device communicating with the controller;
a memory device storing computer executable instructions that, when executed by the controller, cause the controller to perform operations, the operations comprising:
receiving, by the controller and from the ambient pressure detection device, ambient air pressure information indicative of an ambient air pressure external of the medical infusion pump system;
determining if the ambient air pressure information is less than a low limit threshold value or greater than a high limit threshold value;
determining, after determining the ambient air pressure information is less than the low limit threshold value or greater than the high limit threshold value, that the ambient air pressure has stabilized for a pre-specified period of time;
in response to determining that the ambient air pressure has stabilized for the pre-specified period of time, outputting user instructions to inspect a flexible tube that makes up a part of the flow path for bubbles in the medical infusion pump system and to remove the bubbles by flushing.

10. The method of claim 9, the operations further comprising:
in response to determining that the ambient air pressure has stabilized for the pre-specified period of time, outputting additional user instructions to measure a blood glucose level for a user of the medical infusion pump system.

11. The method of claim 9, the operations further comprising:
resuming operation of the medical infusion pump system in response to a user input, and wherein the user input is received by the controller while the ambient air pressure information is indicating that the ambient air pressure is less than the low limit threshold value or greater than the high limit threshold value.

12. The method of claim 9, the operations further comprising:
in response to determining that the ambient air pressure has stabilized for the pre-specified period of time, outputting additional user instructions to replace a medicine cartridge of the medical infusion pump system.

13. The method of claim 9, wherein the low limit threshold value or the high limit threshold value is determined, at least in part, based on a first baseline ambient pressure value, and the operations further comprising:
in response to determining that the ambient air pressure has stabilized for the pre- specified period of time, determining a second baseline ambient pressure based on additional ambient air pressure information indicative of the ambient air pressure external of the medical infusion pump system.

14. The method of claim 9, wherein the user instructions include instructions to disconnect the flexible tube and to flush a portion of the insulin contained by the medical infusion pump system through the flexible tube.

15. The method of claim 9, wherein the user instructions include instructions to a) disconnect the flexible tube from a cannula housing that includes a cannula attached to an underside of the cannula housing and configured to be secured to an infusion site, and b) to flush a portion of the insulin contained by the medical infusion pump system through the disconnected flexible tube.

16. The method of claim 9, wherein the user instructions include instructions to a) disconnect the flexible tube and a cannula housing that includes a cannula attached to an underside of the cannula housing from a skin surface, and b) to flush a portion of the insulin contained by the medical infusion pump system through the disconnected flexible tube.

* * * * *